(12) United States Patent
Jensen et al.

(10) Patent No.: US 7,118,750 B1
(45) Date of Patent: Oct. 10, 2006

(54) MODIFIED TNF-ALPHA MOLECULES, DNA ENCODING SUCH AND VACCINES COMPRISING SUCH MODIFIED TNF-ALPHA AND DNA

(75) Inventors: Martin Roland Jensen, Holte (DK); Søren Mouritsen, Birkerød (DK); Henrik Elsner, Brønshøj (DK); Iben Dalum, Hørsholm (DK)

(73) Assignee: Pharmexa A/S, Horsholm (DK)

( * ) Notice: Subject to any disclaimer, the term of this patent is extended or adjusted under 35 U.S.C. 154(b) by 31 days.

(21) Appl. No.: 09/060,294

(22) Filed: Apr. 15, 1998

Related U.S. Application Data

(60) Provisional application No. 60/044,187, filed on Apr. 24, 1997.

(30) Foreign Application Priority Data

Apr. 15, 1997 (DK) ................................ DK 418/97

(51) Int. Cl.
*A61K 38/19* (2006.01)
*C07K 14/25* (2006.01)

(52) U.S. Cl. .................... 424/192.1; 424/85.1; 930/144

(58) Field of Classification Search .............. 424/185.1, 424/190.1, 192.1; 435/69.7, 325, 252.3, 435/320.1; 536/23.4
See application file for complete search history.

(56) References Cited

U.S. PATENT DOCUMENTS

| 5,580,859 A | 12/1996 | Felgner et al. ................. 514/44 |
| 5,589,466 A | 12/1996 | Felgner et al. ................. 514/44 |

FOREIGN PATENT DOCUMENTS

| EP | 0 251 037 | | 1/1988 |
| EP | 0 619 372 | | 10/1994 |
| WO | WO90/07579 | | 7/1990 |
| WO | WO92/19746 | | 11/1992 |
| WO | WO 93/05810 A1 | * | 4/1993 |
| WO | WO95/05849 | | 3/1995 |

OTHER PUBLICATIONS

Cooke et al. Immunoglobulin signal transduction guides the specificity of B cell-T cell interactions and is blocked in tolerant self-reactive B cells. J Exp Med. Feb. 1, 1994;179(2).*

Werdelin, O, et al, Immunological Reviews, 1988, No. 106, pp. 181-193.
Langstein, H. et al, Cancer Research. vol. 51, 1991, pp. 2302-2306.
Arend, W. et al, Arthritis and Rheumatism, vol. 33, No. 3, Mar. 1990, pp. 305-315.
Elliott, M. et al, LANCET, vol. 344, Oct. 22, 1994, pp. 1105-1110.
van Dullemen, H. et al, GASTROENTEROLOGY, vol. 109, No. 1 (1995), pp. 129-135.
Jones, E. et al, "Crystal Structure of TNF", Tumor Necrosis Factors, Structure, Function and Mechanism of Action, edited by Bharat B. Aggarwal and Jan Vilcek, 1992, Marcel Dekker, Inc, New York, Chapter 5, pp. 92-127.
Smith, R. et al, J. Biol. Chem Crystal Structure of TNF

FIG. 3a

```
   1  cacaccctga  caagctgcca  ggcaggttct  cttcctctca  catactgacc
  51  cacggctcca  ccctctctcc  cctggaaagg  acaccatgag  cactgaaagc
 101  atgatccggg  acgtggagct  ggccgaggag  gcgctcccca  agaagacagg
 151  ggggccccag  ggctccaggc  ggtgcttgtt  cctcagcctc  ttctccttcc
 201  tgatcgtggc  aggcgccacc  acgctcttct  gcctgctgca  ctttggagtg 251  atcggccccc  agagggaaga  gtcccccagg  gacctctctc  taatcagccc
 301  tctggcccag  gcagtcagat  catcttctcg  aaccccgagt  gacaagcctg
 351  tagcccatgt  tgtagcaaac  cctcaagctg  aggggcagct  ccagtggctg
 401  aaccgccggg  ccaatgccct  cctggccaat  ggcgtggagc  tgagagataa
 451  ccagctggtg  gtgccatcag  agggcctgta  cctcatctac  tcccaggtcc 501  tcttcaaggg  ccaaggctgc  ccctccaccc  atgtgctcct  cacccacacc
 551  atcagccgca  tcgccgtctc  ctaccagacc  aaggtcaacc  tcctctctgc
 601  catcaagagc  ccctgccaga  gggagacccc  agaggggggct  gaggccaagc
 651  cctggtatga  gcccatctat  ctgggagggg  tcttccagct  ggagaagggt
 701  gaccgactca  gcgctgagat  caatcggccc  gactatctcg  actttgccga 751  gtctgggcag  gtctactttg  ggatcattgc  cctgtgagga  ggacgaacat
 801  ccaaccttcc  caaacgcctc  ccctgcccca  atccctttat  taccccctcc
 851  ttcagacacc  ctcaacctct  tctggctcaa  aaagagaatt  gggggcttag
 901  ggtcggaacc  caagcttaga  actttaagca  acaagaccac  cacttcgaaa
 951  cctgggattc  aggaatgtgt  ggcctgcaca  gtgaagtgct  ggcaaccact 1001  aagaattcaa  actggggcct  ccagaactca  ctggggccta  cagctttgat
1051  ccctgacatc  tggaatctgg  agaccaggga  gcctttggtt  ctggccagaa
1001  tgctgcagga  cttgagaaga  cctcacctag  aaattgacac  aagtggacct
1151  taggccttcc  tctctccaga  tgtttccaga  cttccttgag  acacggagcc
1201  cagccctccc  catggagcca  gctccctcta  tttatgtttg  cacttgtgat 1251  tatttattat  ttatttatta  tttatttatt  tacagatgaa  tgtatttatt
1301  tgggagaccg  gggtatcctg  ggggacccaa  tgtaggagct  gccttggctc
1351  agacatgttt  tccgtgaaaa  cggaggctga  acaataggct  gttccatgt
1401  agcccctgg   cctctgtgcc  ttcttttgat  tatgttttt   aaaatattat
1451  ctgattaagt  tgtctaaaca  atgctgattt  ggtgaccaac  tgtcactcat 1501  tgctgaggcc  tctgctcccc  agggagttgt  gtctgtaatc  ggcctactat
1551  tcagtggcga  gaaataaagg  ttgcttagga  aagaa
```

FIG. 3b

Amino acid sequence for human TNFα[8]

Accession code: Swissprot P01375

```
 -76 MSTESMIRDV  ELAEEALPKK  TGGPQGSRRC  LFLSLFSFLI  VAGATTLFCL
 -26 LHFGVIGPQR  EEFPRDLSLI  SPLAQA
   1 VRSSSRTPSD  KPVAHVVANP  QAEGQLQWLN  RRANALLANG  VELRDNQLVV
  51 PSEGLYLIYS  QVLFKGQGCP  STHVLLTHTI  SRIAVSYQTK  VNLLSAIKSP
 101 CQRETPEGAE  AKPWYEPIYL  GGVFQLEKGD  RLSAEINRPD  YLDFAESGQV
 151 YFGIIAL
```

Conflicting sequence F−>S at position −14. Disulphide bond between Cys69−101. Signal anchor sequence −41 to −21 (underlined). Myristylation on Lys−58/−57.

Location of inserted epitopes

FIG. 4b

| # | 1 | 11 | 21 | 31 | 41 | 51 | 61 | 71 |
|---|---|---|---|---|---|---|---|---|
| WT | VRSSSRTPSD | KPVAHVVANP | QAEGQLQWLN | RRANALLANG | VELRDNQLVV | PSEGLYLIYS | QVLFKGQGCP | STHVLLTHTI |
| 2-1 | -------Q | YIKANSKFIG | ITEL | | | | | |
| 2-3 | | | | | | | ---QYIKANSKFIGITEL--- | |
| 2-4 | | | | | | | | |
| 2-5 | | | | | | | | ---QYIKA |
| 2-7 | -------F | NNFTVSFWLR | VPKVSASHLE | | | | | |
| 30-1 | | | | | ----F | NNFTVSFWLR | | |
| 30-2 | | | | | | VPKVSASHLE | | |
| 30-3 | | | | | | | --FNNFTVS | |
| 30-4 | | | | | | | | FWLRVPKVSA |
| 30-5 | | | | | | | | |

| # | 81 | 91 | 101 | 111 | 121 | 131 | 141 | 151 |
|---|---|---|---|---|---|---|---|---|
| WT | SRIAVSYQTK | VNLLSAIKSP | CQRETPEGAE | AKPWYEPIYL | GGVFQLEKGD | RLSAEINRPD | YLDFAESGQV | YFGIIAL |
| 2-1 | | | | | | | | |
| 2-3 | | | | | | | | |
| 2-4 | | | | | ---QYIKANS | KFIGITEL--- | | |
| 2-5 | | | | ---QYIKANS | KFIGITEL--- | | | |
| 2-7 | | | | | | ---QYKANSKF | IGITEL--- | |
| 30-1 | NSKFIGITEL | | | | | | | |
| 30-2 | | | | | | | | |
| 30-3 | SHLE--- | | | | | | | |
| 30-4 | | | ---FNNFT | VSFWLRVPKV | SASHLE--- | | | |
| 30-5 | | | | | | ---FNNFTVSFW | LRVPKVSASH | LE--- |

FIG. 5a

TNFα analogs with the P30 epitope inserted

TNF2-1

TNF2-3

TNF2-4

TNF2-5

TNF2-7

FIG. 5b

TNFα analogs with the P30 epitope inserted

TNF30-1

TNF30-2

TNF30-3

TNF30-4

TNF30-5

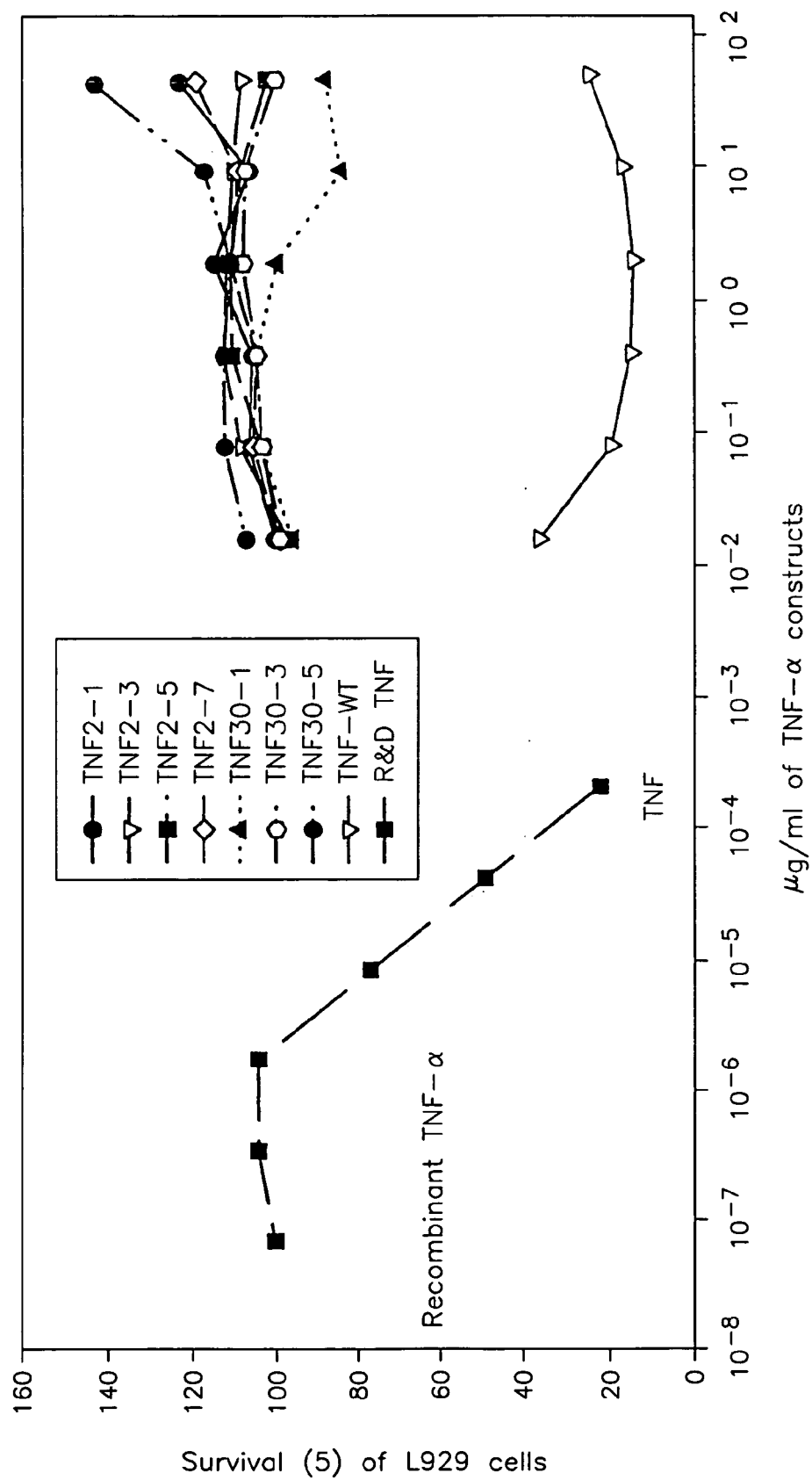

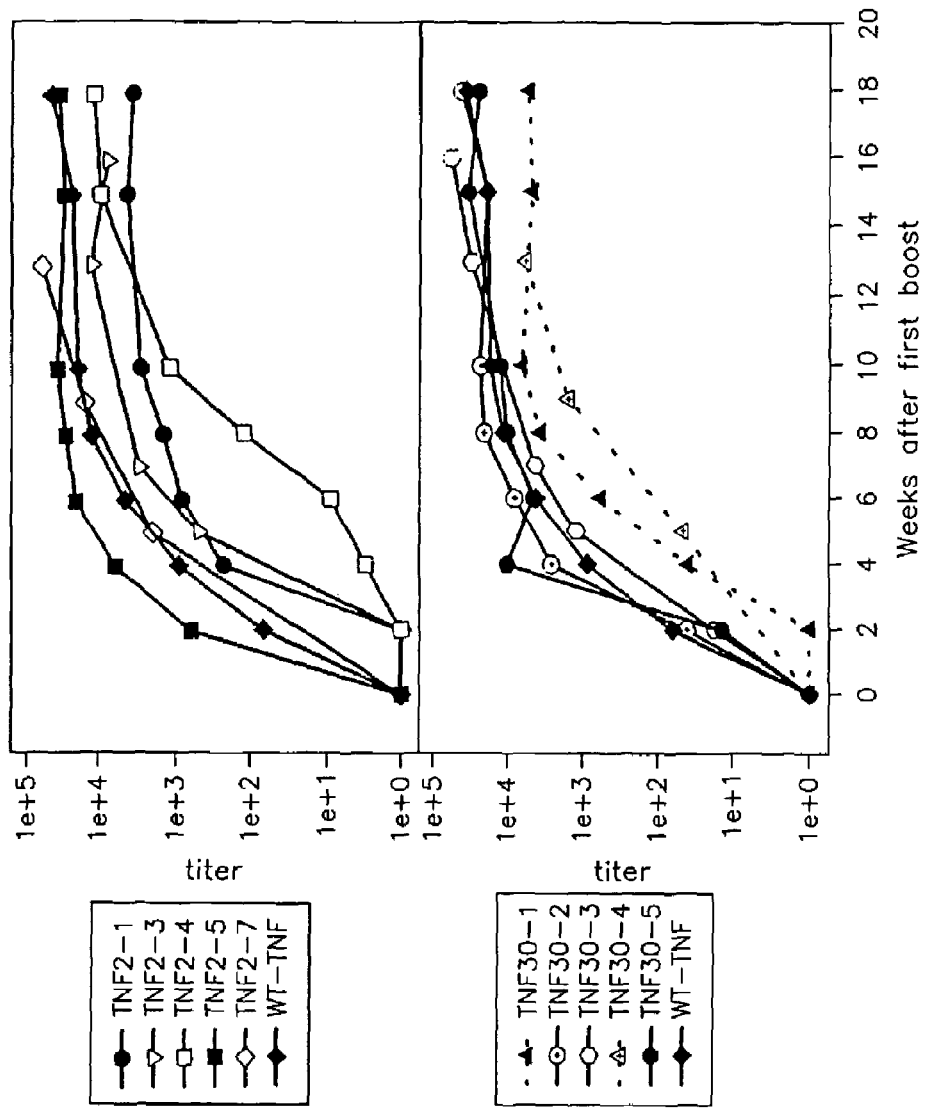

The ability of P2/P30 modified human TNFα molecules to induce neutralizing antibodies as measured in The ability of P2/P30 modified human TNFα molecules to induce neutralizing antibodies as

FIG. 16
Mutation Strategy
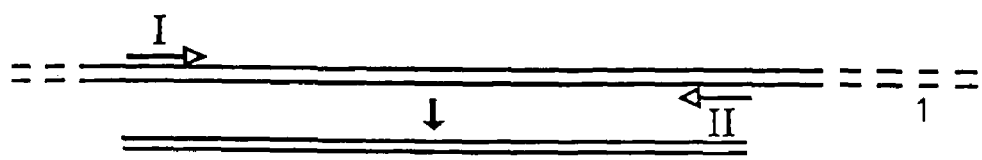
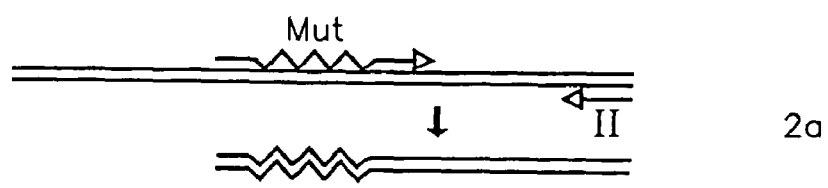
2a
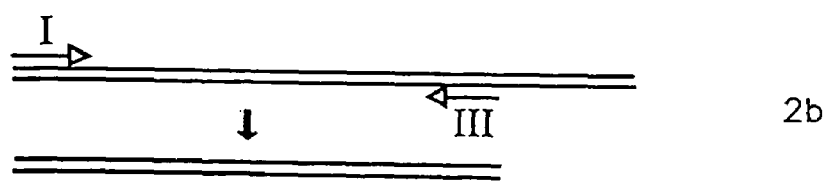
2b
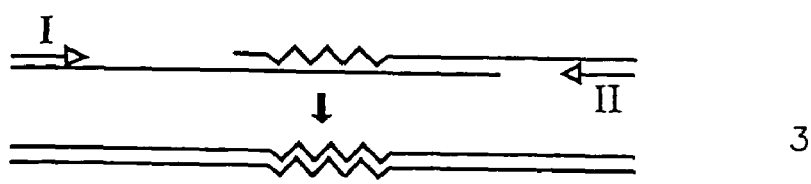
3

MODIFIED TNF-ALPHA MOLECULES, DNA ENCODING SUCH AND VACCINES COMPRISING SUCH MODIFIED TNF-ALPHA AND DNA

This application claims the benefit of U.S. Provisional Application No. 60/044,187, filed 24 Apr. 1997.

FIELD OF THE INVENTION

The present invention relates to human cytokine Tumor Necrosis Factor α (TNFα) molecules which has been modified so that they are capable of raising neutralizing antibodies towards unmodified human TNFα following administration of the modified TNFα molecule to the human host. The invention also relates to human TNFα vaccines based on said modified TNFα molecules. Further aspects of the invention will appear from the discussion below.

BACKGROUND OF THE INVENTION

Physiologically, the vertebrate immune system serves as a defense mechanism against invasion of the body by infectious objects such as microorganisms. Foreign proteins are effectively removed via the reticuloendothelial system by highly specific circulating antibodies, and viruses and bacteria are attacked by a complex battery of cellular and humoral mechanisms including antibodies, cytotoxic T lymphocytes (CTL), natural killer cells (NK), complement, etc. The leader of this battle is the T helper ($T_H$) lymphocyte which, in collaboration with the Antigen Presenting Cells (APC), regulate the immune defense via a complex network of cytokines.

$T_H$ lymphocytes recognize protein antigens presented on the surface of the APC. They do not recognize, however, native antigen per se. Instead, they appear to recognize a complex ligand consisting of two components, a "processed" (fragmented) protein antigen (the so-called T cell epitope) and a Major Histocompatibility Complex class II molecule (O. Werdelin et al., 1 mm. Rev. 106, 181 (1988)). This recognition eventually enables the $T_H$ lymphocyte specifically to help B lymphocytes to produce specific antibodies towards the intact protein antigen (Werdelin et al., supra). A given T cell only recognizes a certain antigen-MHC combination and will not recognize the same or another antigen presented by a gene product of another MHC allele. This phenomenon is called MHC restriction.

Fragments of self-proteins are also presented by the APC, but normally such fragments are ignored or not recognized by the T helper lymphocytes. This is the main reason why individuals generally do not harbour autoantibodies in their serum eventually leading to an attack on the individual's own proteins (the so-called self- or autoproteins). However, in rare cases the process goes wrong, and the immune system turns towards the individual's own components, which may lead to an autoimmune disease.

The presence of some self-proteins is inexpedient in situations where they, in elevated levels, induce disease symptoms. Thus, tumour necrosis factor α (TNFα) is known to be able to cause cachexia in cancer patients and patients suffering from other chronic diseases (H. N. Langstein et al. Cancer Res. 51, 2302–2306, 1991). TNFα also plays important roles in the inflammatory process (W. P. Arend et al. Arthritis Rheum. 33, 305–315, 1990) and neutralization of TNFα by the use of monoclonal antibodies has thus been demonstrated to be beneficial in patients with chronic inflammatory diseases such as rheumatoid arthritis, Elliott et al., Lancet 1994, 344:1105–10 and Crohn's disease, van Dullemen et al., Gastroenterology 109(1):129–135(1995). There is therefore a need for a method for the induction of neutralizing antibodies against such TNFα proteins, and the present invention comprises a vaccine against TNFα which provide this property.

Tumour Necrosis Factor

1. General Background

Tumour necrosis factor (TNF) is a member of the cytokine family of regulatory proteins (see Walsh, G. and Headon, D. E., Protein Biotechnology, 1994, John Wiley & Sons Ltd.

England, p. 257–267). Two forms of TNF are now recognized, TNFα and TNFβ, respectively. Although both proteins bind the same receptors and elicit broadly similar biological responses, they are distinct molecules and share less than 30% homology. The original protein termed tumour necrosis factor, referred to as TNF, is more properly termed TNFα; it is also known as cachectin. TNFβ is also referred to as lymphotoxin.

TNFα is produced by a wide variety of cell types, most notably activated macrophages, monocytes, certain T lymphocytes and NK cells, in addition to brain and liver cells. The most potent known inducer of TNTα synthesis, is a complex biomolecule termed lipopolysaccharide. It contains both lipid and polysaccharide components, and is also referred to as endotoxin. Lipopolysaccharide itself is devoid of any anti-tumour activity. The serum of animals injected with lipopolysaccharide was found to contain a factor toxic to cancerous cells, and this factor, produced by specific cells in response to lipopolysaccharide, was termed tumour necrosis factor. Various other agents such as some viruses, fungi and parasites also stimulate the synthesis and release of this cytokine. Furthermore, TNFα may act in an autocrine manner, stimulating its own production.

Native human TNFα is a homotrimer, consisting of three identical polypeptide subunits tightly associated around a threefold axis of symmetry as will be further explained below. This arrangement resembles the assembly of protein subunits in many viral capsid proteins. The individual polypeptide subunits of human TNFα are non-glycosylated and consist of 157 amino acids. The molecule has a molecular weight of 17300 Da and contains a single intrachain disulphide linkage. Human TNFα is synthesized initially as a 233 amino acid precursor molecule. Proteolytic cleavage of the -76 to -1 presequence including a signal sequence releases native TNFα. TNFα may also exist in a 26000 Da membrane-bound form. Three TNFα monomeric subunits associate noncovalently to form a trimer as further explained below.

TNFα induces its biological effects by binding specific receptors present on the surface of susceptible cells. Two distinct TNFα receptors have been identified. One receptor (TNF-R55) has a molecular weight of 55000 Da, whereas the second receptor (TNF-R75) has a molecular weight of about 75000 Da. These two distinct receptor types show no more than 25% sequence homology. TNF-R55 is present on a wide range of cells, whereas the distribution of the TNF-R75 receptor is more limited. Both are transmembrane glycoproteins with an extracellular binding domain, a hydrophobic transmembrane domain and an intracellular effector domain.

The exact molecular mechanisms by which TNFα induces its biological effects remain to be determined. Binding of TNFα to its receptor seems to trigger a variety of events mediated by G-proteins in addition to the activation of adenylate cyclase, phospholipase $A_2$ and protein kinases.

The exact biological actions induced by TNFα may vary from cell type to cell type. Other factors, such as the presence of additional cytokines, further modulate the observed molecular effects attributed to TNFα action on sensitive cells.

The TNFα gene has been cloned and inserted in a variety of recombinant expression systems, both bacterial and eukaryotic. The resultant availability of large quantities of purified, biologically active TNFα has facilitated clinical evaluation a number of diseases, most notably cancer. Many such trials, using TNFα either alone or in combination with interferons, yielded, however, very disappointing results. Large quantities of TNFα can not be administered to patients owing to its toxic—if not lethal—side-effects.

As mentioned above prolonged production of inappropriately elevated levels of TNFα has also been implicated in the development of cachexia, the wasting syndrome often associated with chronic parasitic or other infections, and with cancer. TNFα is also involved in the metastasis and growth of certain tumours as well as in induction of anaemia. Furthermore, TNFα is also directly involved in the development of certain chronic inflammatory disorders in humans, including rheumatoid arthritis and Crohn's disease where administration of monoclonal anti-TNFα antibodies has been shown to be beneficial. TNFα is also involved in osteoporosis and Psoriasis. In addition, it has been shown in animal models that administration of anti-TNFα antibodies may decrease or prevent rejection of grafted or transplanted tissues Imagawa et al, Transplantation 51(1):57–62(1991).

2. Structure of TNFα

I. Introduction

The three-dimensional structure of human tumour necrosis factor (TNFα) has been solved (see "Tumor Necrosis Factors, Structure, Function and Mechanism of Action" edited by Bharat B. Aggarwal and Jan Vilcek, 1992 Marcel Dekker, Ind., New York, Chapter 5 "Crystal structure of TNFα", by Jones, E. Y. Stuart, D. I. and Walker N. P. C.). The biological action of TNFα is dependent on its interaction with its receptors. These interactions are governed by the precise arrangement of the correctly folded tertiary structure. Thus, to understand how the TNFα molecule performs its biological function at the level of amino acid interactions, one must not only know the amino acid sequence, but also the three-dimensional structure.

II. Three-Dimensional Structure

Biologically active TNFα has been shown by analytical ultracentrifugation, small angle x-ray scattering, and gel electrophoresis to be in a trimer conformation in solution, and cross-linking studies have indicated that this is the active form of the protein (Smith and Baglioni, 1987). Analysis of circular dichroism spectra placed TNFα in the all-sheet class of proteins (Wingfield et al., 1987; Davis et al., 1987). Several different crystal forms have been reported for human recombinant TNFα. All the reported crystal forms exhibit crystallographic and/or non-crystallographic threefold symmetry indicative of the presence of TNFα as a trimer within the crystal.

The TNFα trimers lie in loosely packed arrays perforated by 100 Å diameter solvent channels. Only a small proportion of the molecular surface is involved in crystal packing contacts. Such contacts could slightly perturb a few side chains and perhaps even short portions of inherently flexible main chain from their preferred solution conformations.

A. Main-Chain Fold of the TNFα Monomer

The overall shape of a single 157-amino-acid subunit of the TNFα trimer is wedgelike with a height of approximately 55 Å and a maximum breadth of 35 Å near the base. The main-chain topology is illustrated in FIGS. 1a–c; it is essentially a β-sandwich structure formed by two antiparallel β-pleated sheets. The main-chainfold conforms to that of the classic jellyroll motif (FIG. 1c) (Richardson, 1981). The nomenclature adopted in FIG. 1 for the labels of the secondary structural units follows the established convention for viral structures. The standard eight β-strands (B to I) are all present but with an insertion between B and C that adds a short strand onto the edge of both β-sheets and truncates the N-terminal half of C, so that each β-pleated sheet contains five antiparallel β-strands, the back β-sheet comprising β-strands B', B, I, D and G and the front sheet comprising β-strands C', C, H, E and F.

The N terminus is highly flexible. This region, as far as residue 10 (see FIG. 1b), is rather independent of the rest of the molecule, with the first few residues free to sample a variety of conformations in the solvent. In contrast, the C terminus is embedded in the base of the back β-sheet and forms an integral part of this relatively flat secondary structural unit. The gradation in β-strand lengths and the insertion between β-strands B and C conspire to produce a front surface formed almost entirely of loops, and it is this "masked" side of the β-sandwich, which in the trimer is presented to the solvent. The crystallographic data yield a measure of the relative flexibility of the various parts of the structure. The β-strands form a fairly inflexible scaffold; in particular, the back β-sheet is situated at the core of the trimer and consequently is particularly rigid. As would be expected, it is the loops that adorn the outer solvent-accessible surface of the molecule, which exhibit high levels of flexibility/mobility. Overall, there is a general decrease in rigidity as the core becomes more loosely packed in the upper half of the molecule.

B. General Topology of the TNFα Trimer

Three TNFα monomeric subunits associate noncovalently to form a compact, conical trimer having a length of about 55 Å and a maximum breadth of 50 Å. The β-strands of the three individual β-sandwiches lie approximately parallel (the tilt is about 30°) to the threefold axis of the trimer. The interaction between subunits related by the three-fold axis is through a simple edge-to-face packing of the β-sandwich; the edge of the β-sandwich, consisting of strands F and G from one subunit, lies across the back β-sheet [GDIBB'] of a threefold related subunit (see FIG. 2). The carboxy termini lie close to the threefold axis.

The edge-to-face mode of packing produces an extremely tight association between the subunits. Thus the core of the trimer is completely inaccessible to solvent.

C. Amino Acid-Type Distribution

The overall distribution of residue types in the three-dimensional structure of TNFα echoes the general rule for proteins: namely, that hydrophobic residues cluster in the core of the molecule while charged residues decorate the surface. Thus the core of the TNFα sandwich has the expected filling of tightly intercalating large apolar residues.

The energetics of the system do not favour the existence of TNFα in a monomeric state. For a large interface area composed of complementary residues (e.g., polar residues matched against polar residues) the loss of solvent-accessible surface area confers a considerable energetic advantage to formation of the oligomer (i.e., the trimer). The exposure to solvent of the large patch of strongly hydrophobic residues normally buried in the lower portion of the trimeric interface would also act to destabilize the TNFα monomer.

3. Probes of Structure-Function

A. TNFα/Antibody Interactions

It has been observed that antibodies raised against TNFα from one species (e.g., human) do not cross-react with TNFα from another species (e.g., mouse) despite a sequence identity in excess of 80% and the ability of TNFα to bind to the TNFα receptors of other species. If the degree of sequence variation is mapped onto the three-dimensional structure, it is immediately apparent that the most sequence-variable regions of the molecule correspond to the antibody-accessible surface loops. The regions of highly conserved residues within the sandwich or at the trimeric interface are effectively invisible to antibodies. Thus the epitope for an antibody against TNFαwill always contain some residues that will vary between species, thus abolishing antibody binding. This implies that the characteristics of the interaction between TNFα and its receptor must somehow differ from those required for binding of an antibody to TNFα.

B. Site-Directed Mutagenesis

The role of various specific residues and regions of the TNFα molecule with regard to its biological (cytotoxic) activity and receptor binding has been probed by replacement of those residues by different amino acids or deletion of part of the sequence using the techniques of site-directed mutagenesis (Jones et al, p. 113–119).

The deletion of up to eight residues from the N-terminus without any deleterious effect on biological activity serves to emphasize the nonessential nature of this region for overall molecular stability. N-terminal residues appear to exert an indirect, second-order effect on the biological efficacy of the TNFα trimer.

Non-conservative substitutions of the normally highly conserved residues which form the tightly packed core of the β-sandwich distort the structure and hence abrogate the biological activity of TNFα (Yamagishi et al., 1989). Many such mutated proteins fail to form a stable, correctly folded molecule. Some conservative substitutions are permitted within the hydrophobic patch at the bottom of the threefold axis; however, there appears to be much greater leeway in the more loosely packed region near the top of the trimer. In particular, Cys 69 and Cys 101, which form the disulphide bridge between two connecting loops at the loosely packed top of the molecule, are relatively insensitive to changes (see FIG. 1a). Generally, however, in order to retain some biological activity of TNFα the mutations near the central axis of TNFαmust be highly conservative, preserving the overall shape of TNFα.

The residues on the surface of the molecule have a considerably greater freedom to mutate without incurring disastrous structural penalties as witnessed by the proliferation of variations of residues in this category between species. Thus drastic reductions in biological activity of TNFα due to substitutions in this area points to the direct involvement of such residues in the functional interaction of the TNFα trimer with its receptor. Residues comprising Arg 31, Arg 32 and Ala 33 situated in the connecting loop between the B and B' strand of the back β sheet, Ser 86 and Tyr 87 situated in the connecting loop between the E and F strands of the front β-sheet, and Glu 146 situated in the connecting loop between the H strand of the front β sheet and the I-strand of the back β-sheet appear to be such amino acid residues (see FIG. 3). They appear to fall into two distinct regions on the front and the back sides of the TNFα monomer. The distribution of all deleterious mutations regardless of structural category further reinforces this picture. The existence of these "hot spots" for sensitivity of biological function to mutation has been reviewed by Yamagishi et al. (1989) and Goh et al. (1990).

4. Summary

A rich variety of data may now be brought to bear on the specific relationship of structure to function for TNFα. All available evidence points to the importance of the trimer as the stable natural unit. It is apparent that the two hotspot regions situated on separate sides of the TNFα monomer are brought close to each other in terms of neighbouring subunits in the trimer. Thus a region of functional importance consisting of residues 31 to 35, 84 to 87, and 143 to 148 appears to be located at the interface between two subunits on the lower half of the trimer. Yamagishi et al. (1989) report loss of receptor binding ability as well as cytotoxicity for the mutation of Asp 143 to Tyr, and Tsujimoto et al. (1987) report a similar effect for Arg 31 and Arg 32 to Asn and Thr. Thus the site may be associated directly with receptor binding as well as cytotoxicity. It is interesting that the receptor binding region of TNFα appears to lie at the interface between two subunits.

In summary, the detailed three-dimensional structure for TNFα serves to explain a wide range of observations on antibody binding, oligomerization, and site-directed mutagenesis. When the structure is considered in combination with recent, extensive site-directed mutants, a region of biological importance with regard to receptor binding is apparently at the subunits on the lower half of the trimer.

DESCRIPTION OF THE PRIOR ART

In WO 95/05489 the present inventors disclose a method for the modification of self-proteins so as to induce antibody response against the unmodified self-protein, wherein a self-protein analog is provided by molecular biological means. More specifically one or more peptide fragments of the self-protein are substituted by one or more immunodominant, foreign T-cell epitopes.

It is stated as preferable in WO 95/05489 that the immunodominant T-cell epitope is inserted so that flanking regions from the original protein comprising at least 4 amino acids are preserved on either side of the inserted epitope. In other words the epitope should not be combined with the self-protein as a fusion protein. Apart from that no specific guidance is provided as to the optimal intramolecular position of the inserted epitope in order to create the most powerful antibody response against the unmodified self-protein. Presumably, this will vary from self-protein to self-protein but based on the general guidance in the specification the most appropriate position(s) can be determined without undue experimentation by selecting peptides comprising appropriate immunodominant epitopes, exchanging peptide sequences of essentially the same length in various parts of the self-protein molecule and determining the raised antibody response by suitable assay techniques.

The insertion between β strands B and C is shown in dashed lines; the connection between B and C would run straight across at the top of the molecule.

Figure 2:
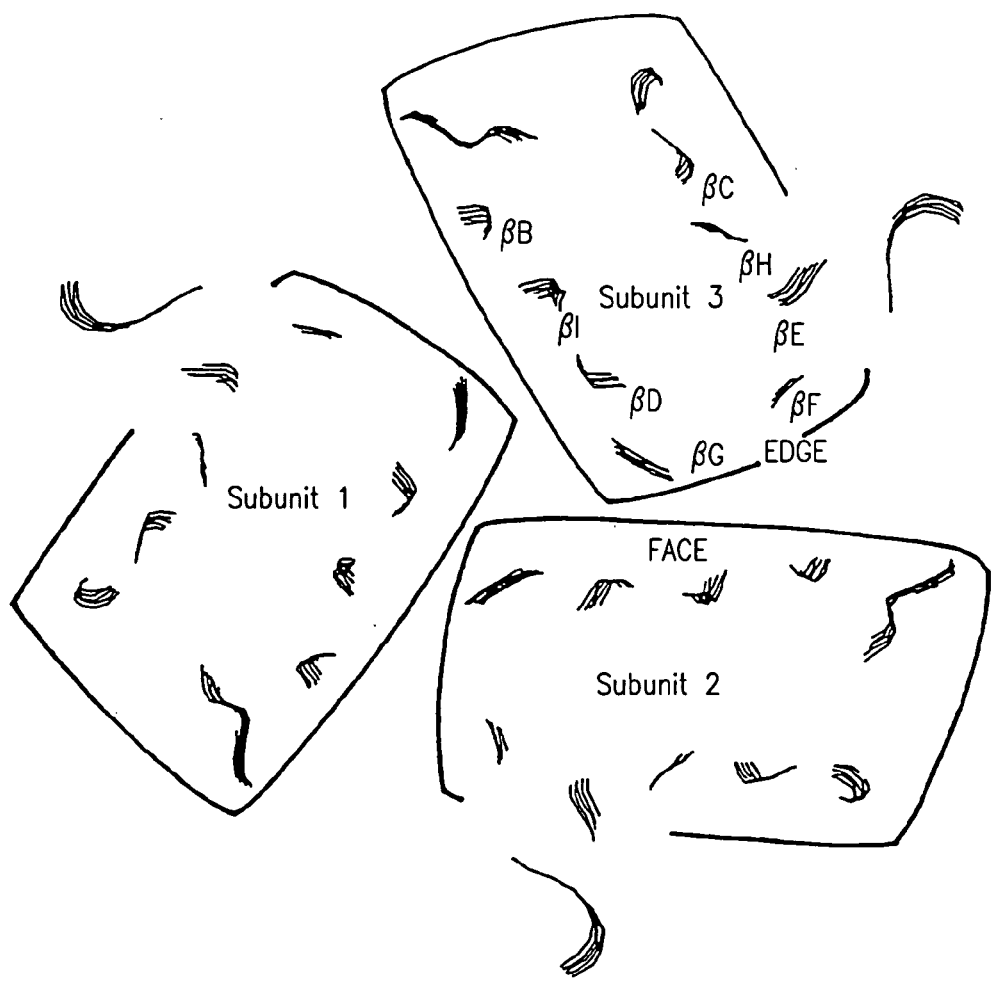

FIG. 2 shows the edge-to-face packing of β sandwiches in the TNF trimer. The view, down the threefold axis, shows a narrow slab of the trimer with β strands represented by ribbons running into and out of the page.

FIG. 3(a) (SEQ ID NO:43) illustrates the DNA sequence encoding tumor necrosis factor (TNFα) having the amino acid sequence shown in FIG. 3(b).

The DNA sequence is available from Gen Bank under accession no. M10988, SEQ ID NO:339737.

The sequence has been described by Wang et al., Science 228, 149–154 (1985). The sequence includes codons encoding the -76–-1 presequence of human TNFα.

The complete gene sequence including introns has been described by Nedwin et al., Nucleic Acids, Res. 13(17) 6361–6373 (1985), Shirai et al., Nature 313(6005), 803–806 (1985) and Dennica et al., Nature 312 (5996), 724–729 (1984).

FIG. 3(b) (SEQ ID NO: 44) shows the amino acid sequence of human TNFα including the -76–-1 presequence.

Figure 4A:
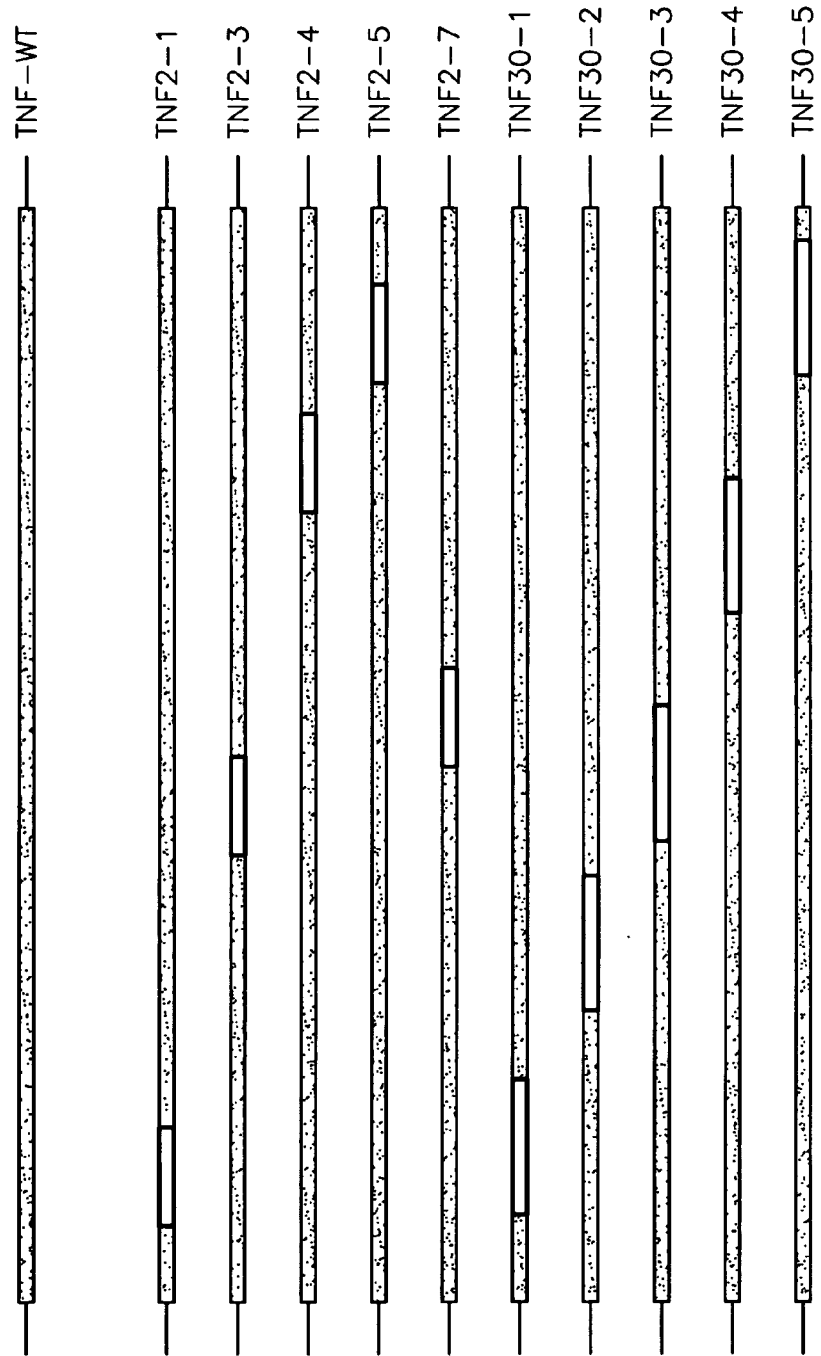

FIG. 4(a) schematically illustrates the substitutions of immunodominant epitopes P2 and P30 in a wild type TNFα (WT) to form the TNFα analogs TNF2-1 SEQ. ID. NO. 1 to 2-7 SEQ. ID. NO. 9 and TNF30-1 SEQ. ID. NO. 11 to 30-5 SEQ. ID. NO. 19.

FIG. 4(b) shows the exact locations of the substitutions in the WT sequence for the individual TNFα analogs.

Figure 1A:
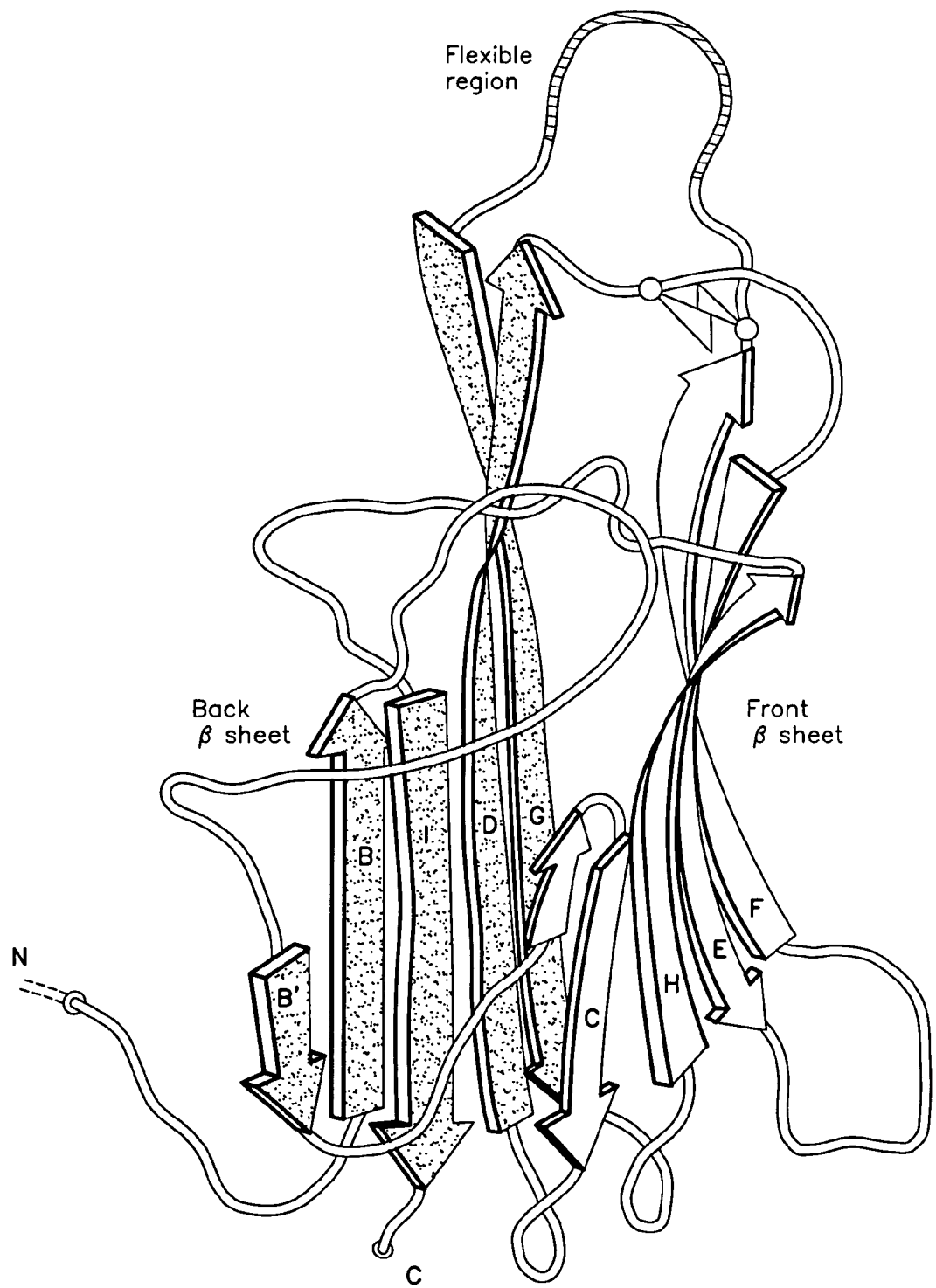
FIG. 1(a) illustrates the crystal structure of native TNFα monomer. The figure is a diagrammatic sketch of the subunit fold, β strands are shown as thick arrows in the amino-to-carboxy direction and connecting loops are depicted as thin lines. The disulfide bridge is denoted by a lightning flash and a region of high flexibility is crosshatched. The trimer threefold axis would be vertical for this orientation.
Figure 1B:
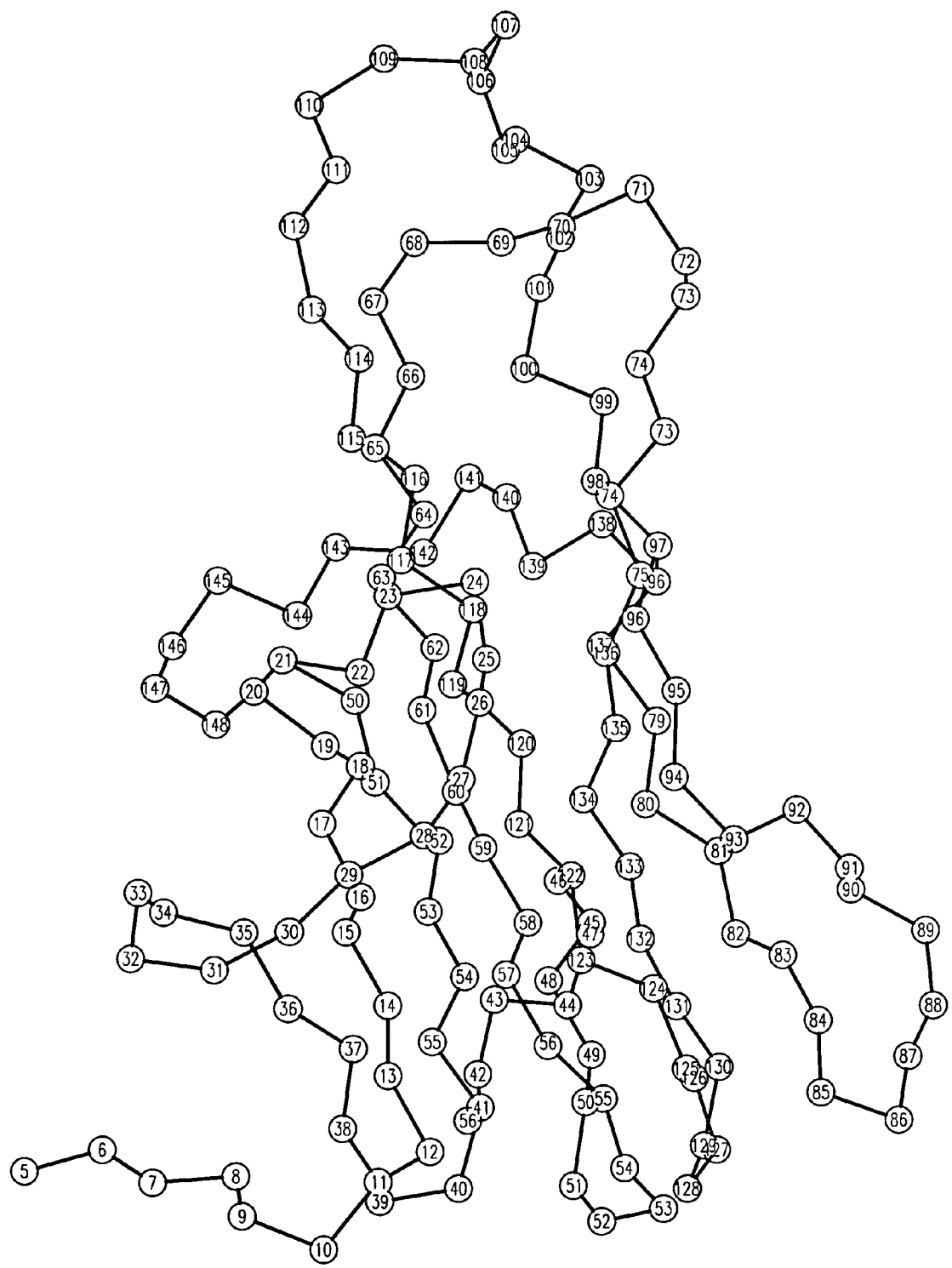
FIG. 1(b) is a Cα chain trace of the TNFα monomer crystal structure. This detailed representation should be used in conjunction with FIG. 1(a) to give the precise alignment of the amino acid sequence with the clearer but stylized representation of the subunit fold.
Figure 1C:
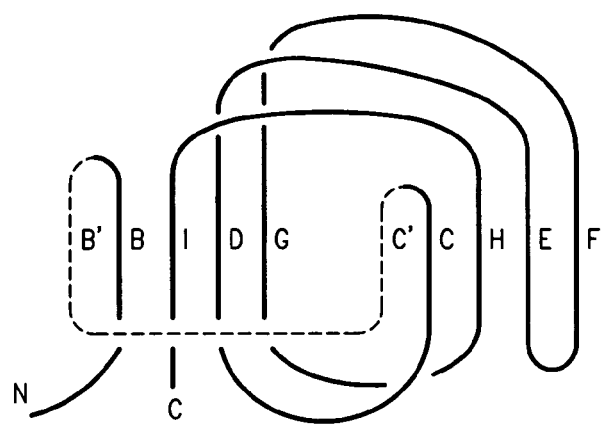
FIG. 1(c) shows the TNFα structure as a jelly roll motif.

FIGS. 5(a) and 5(b) show the structure of the analogs based on FIG. 1(a), where the individual substitutions by P2 and P30 in the strands of the β-sheets and the connection loops, respectively, are marked in black.

FIG. 6 shows the biological activity of the TNFα analogs in the L929 assay compared with recombinant TNFα.

FIG. 7 shows the anti-human TNFα antibody response in rabbits to vaccination with the modified TNFα molecules in rabbits.

Figure 8:
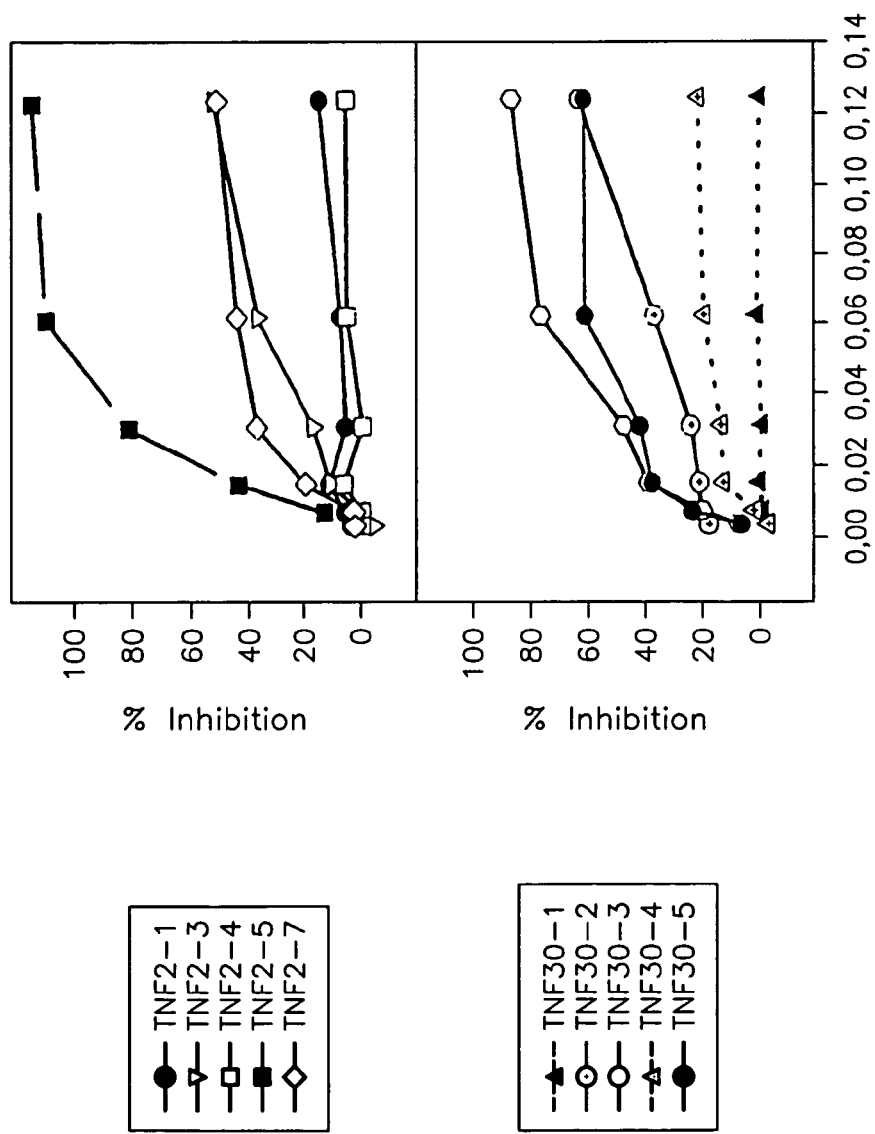

FIG. 8 shows the ability of P2/P30 modified human TNFα molecules to induce neutralizing antibodies as measured in the L929 cell assay.

Figure 9:
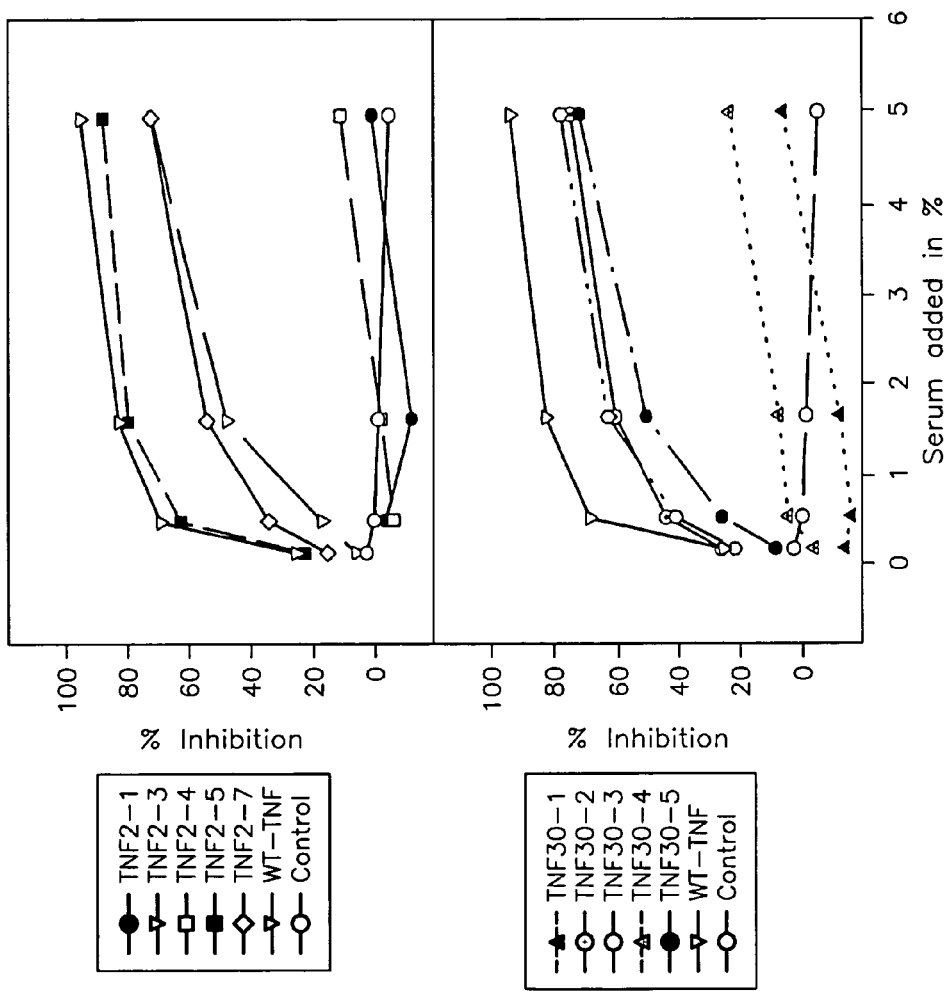

FIG. 9 shows the ability—when administered to rabbits—of P2/P30 modified human TNFα molecules to induce neutralizing antibodies as measured in receptor assay.

Figure 10:
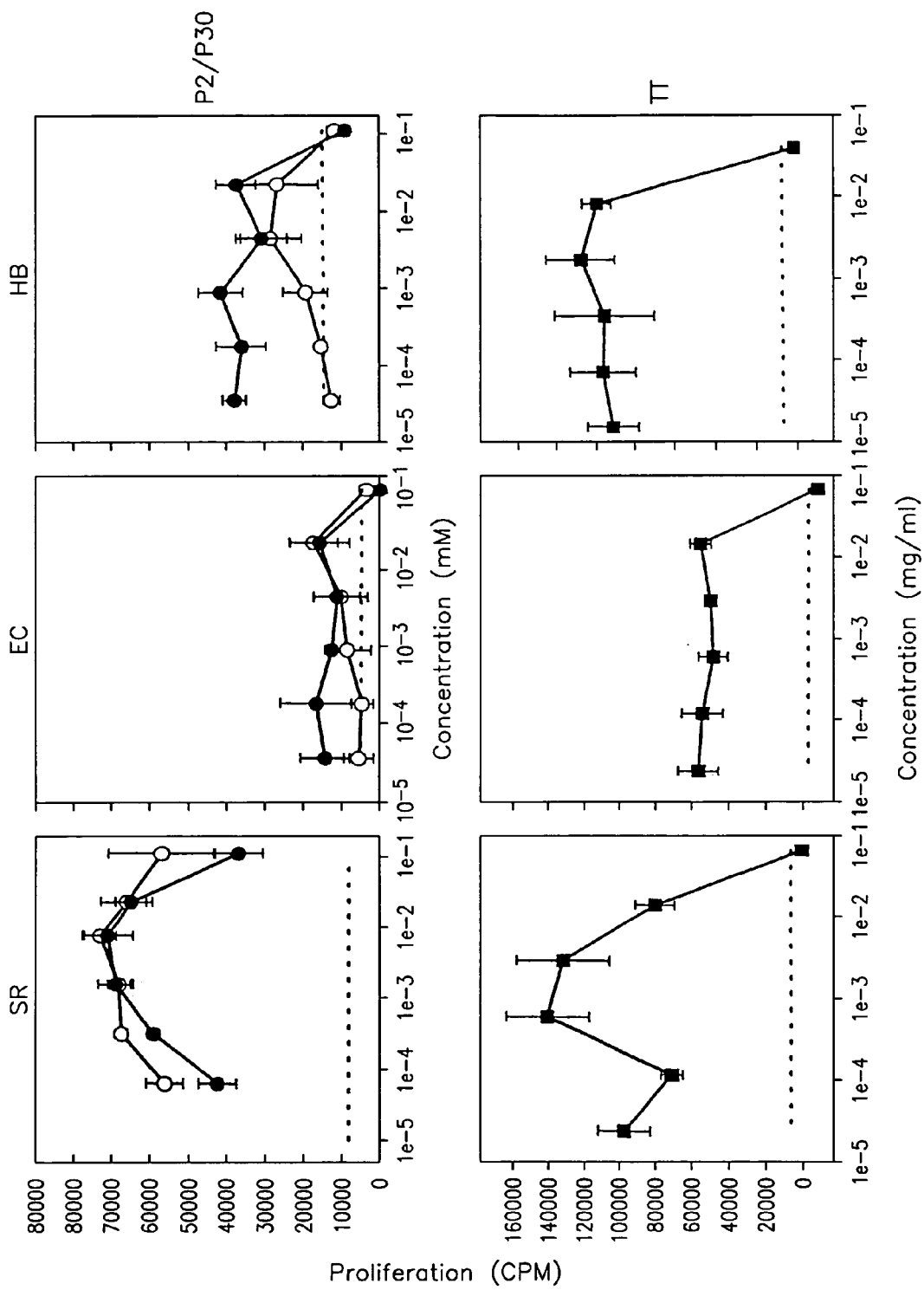

FIG. 10 shows the Peripheral Blood Mononuclear Cell (PBMC) response in three donors towards TT and the P2 and P30 peptides.

Figure 11:
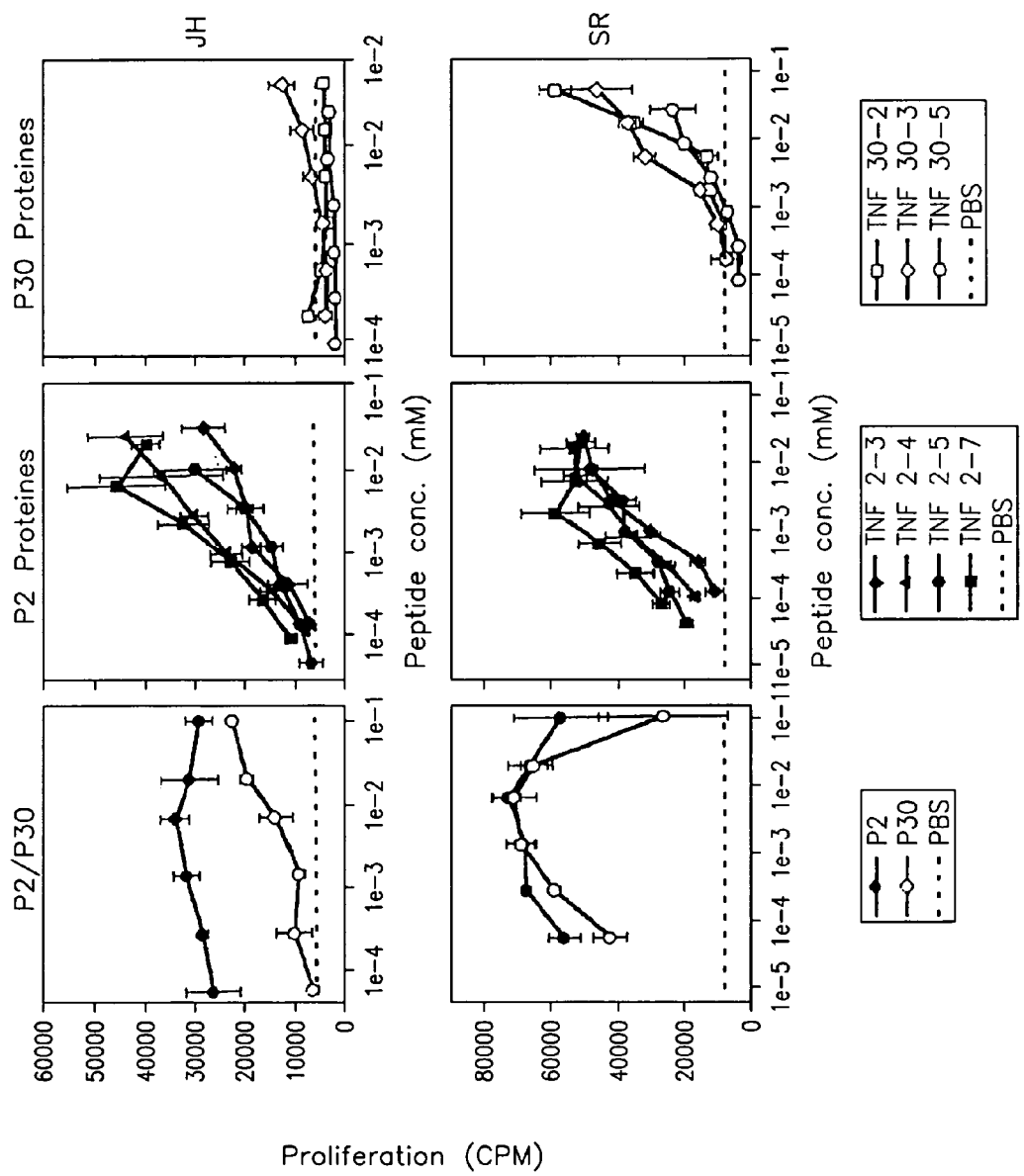

FIG. 11 shows the polyclonal proliferation response in two donors using the different P2 and P30 modified TNFα molecules.

Figure 12:
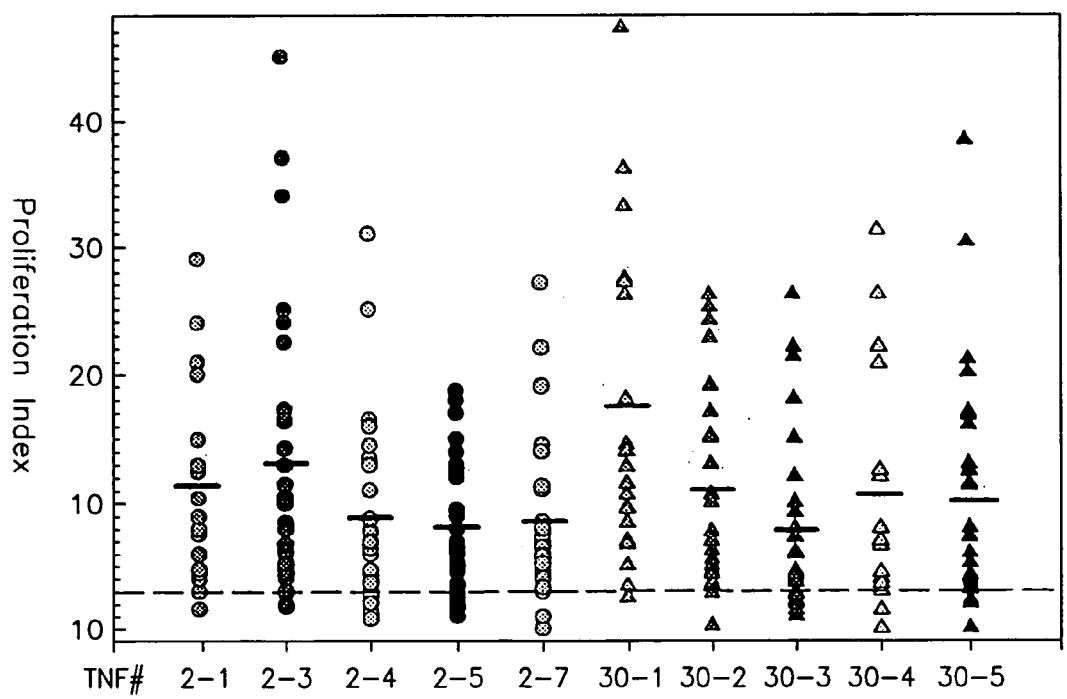

FIG. 12 shows the Proliferation Indexes (PIs) calculated from 34 experiments for the P2 and P30 modified TNFα molecules.

Figure 13:
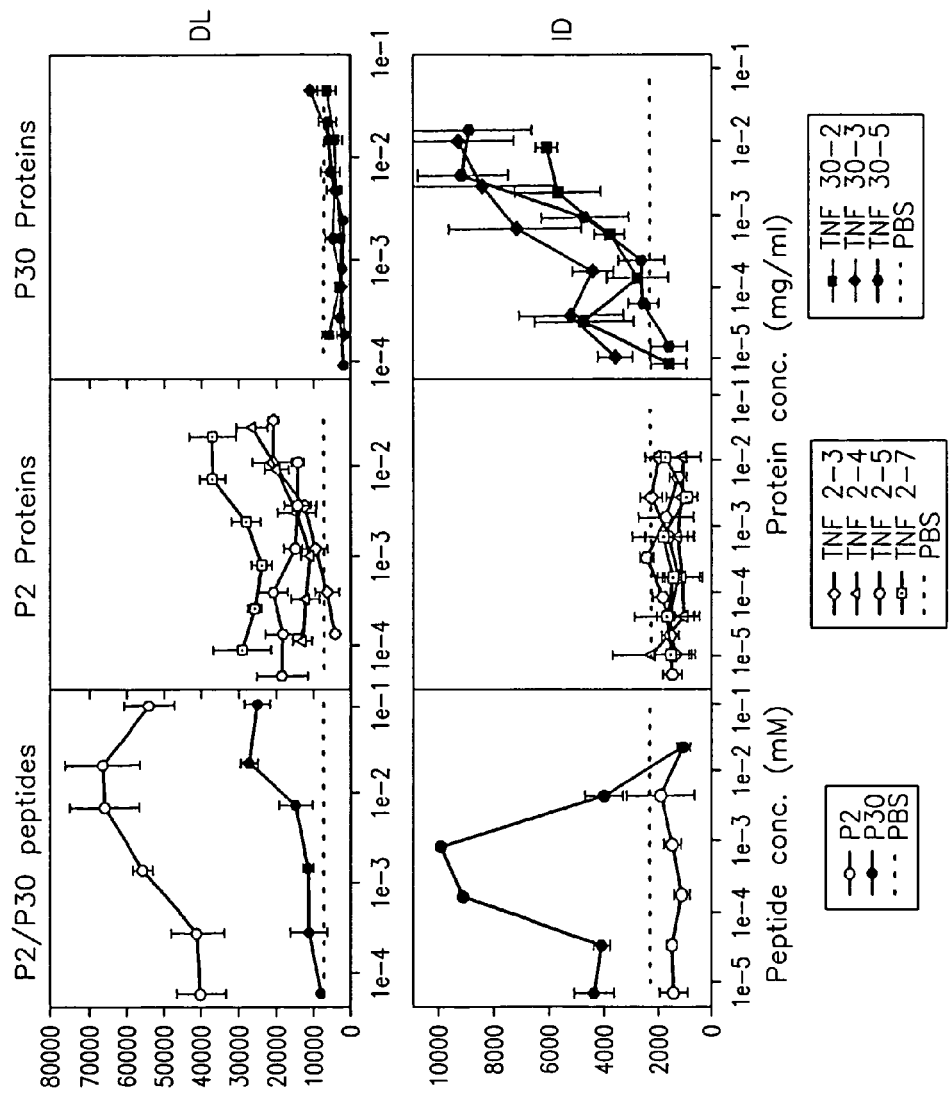

FIG. 13 shows the PBMC response against P2 and P30 modified TNFα proteins in P2 and P30 specific responders, respectively.

Figure 14:
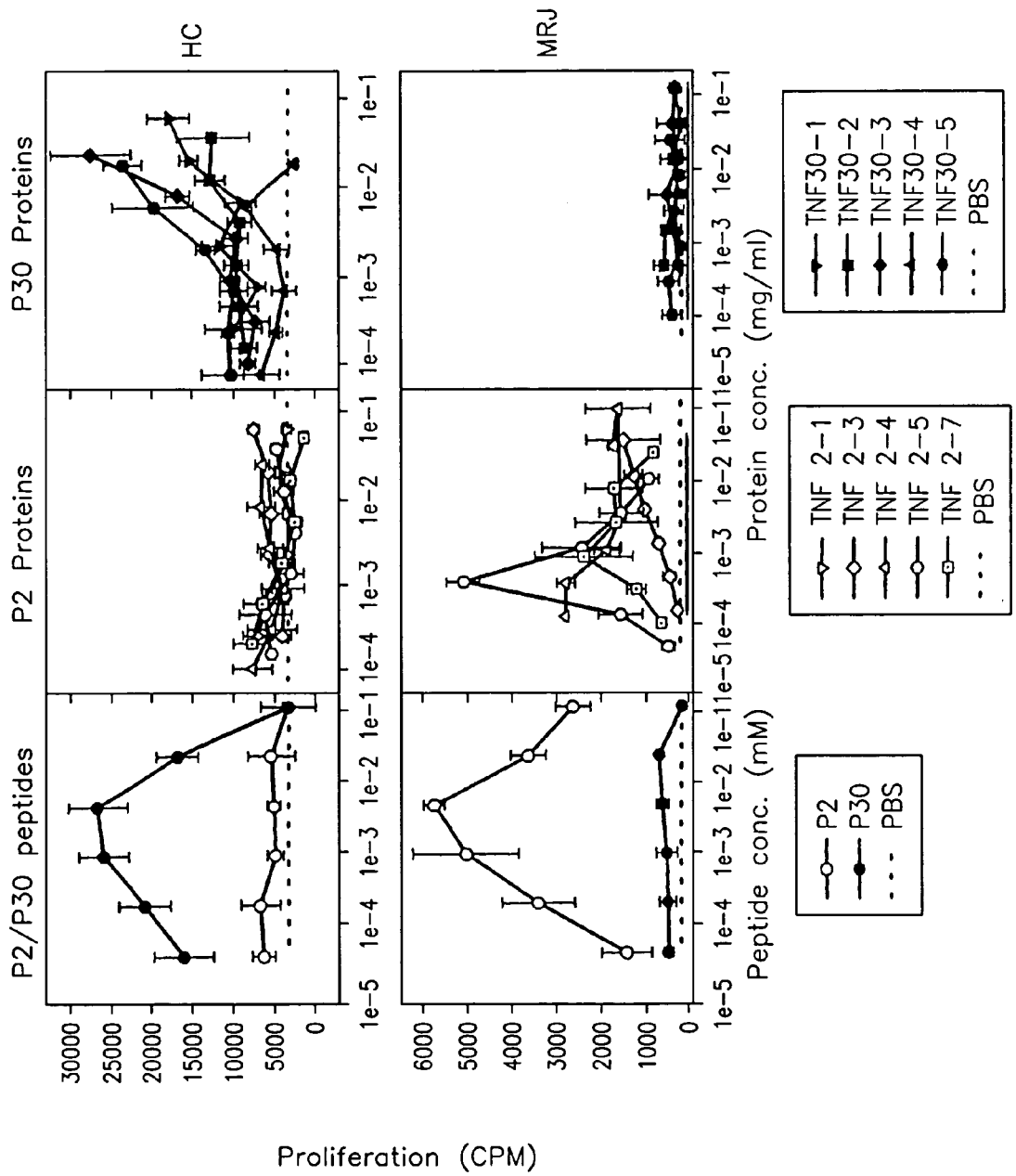

FIG. 14 shows a similar PBMC response in two other donors.

Figure 15:
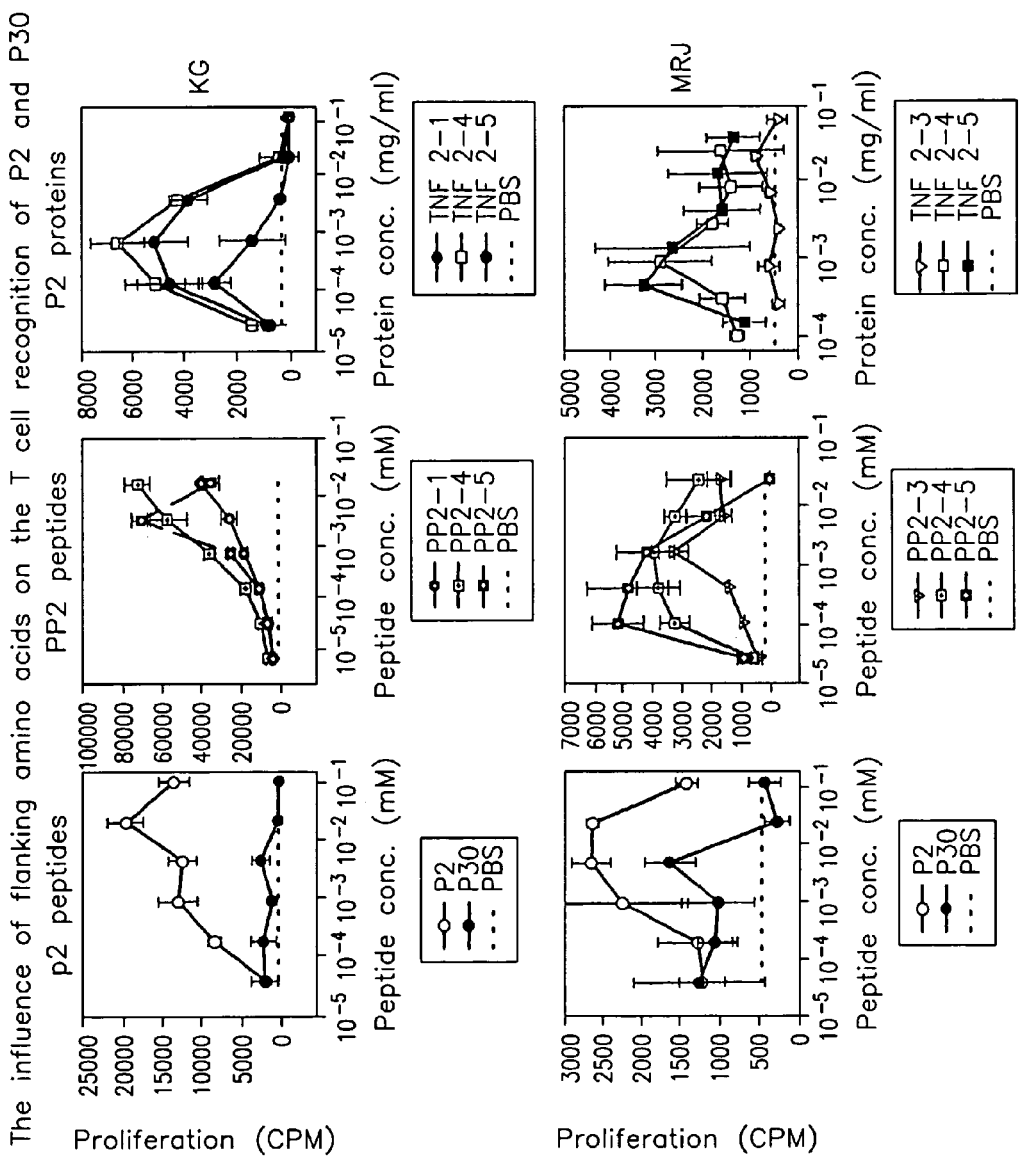
Figure 1A:
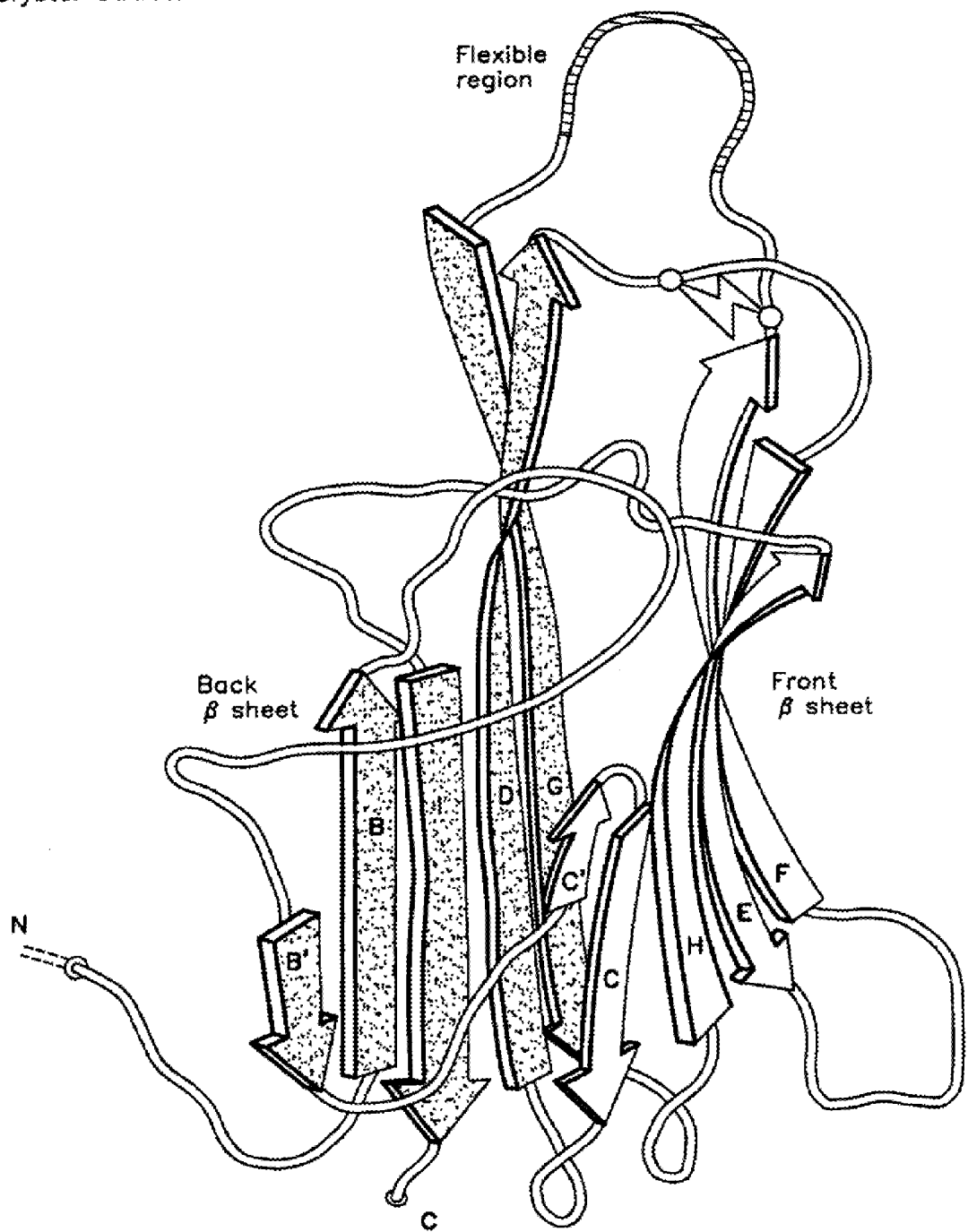

FIG. 15 shows the influence of flanking amino acids on the T cell recognition of P2 and P30.

FIG. 16 shows the mutation strategy used for the preparation of the modified TNFα molecules.

SUMMARY OF THE INVENTION

The purpose of the present invention is to provide guidelines as to how a particular self-protein within the general scope of the above-mentioned WO 95/05489, viz. human TNFα should be modified in order to be biologically inactive as well as be able to induce a strong neutralizing antibody response towards unmodified, biologically active TNFα. In the present context "biologically inactive" refers to the activities of the unmodified TNFα, mainly its cytotoxic activity.

From the discussion of the tertiary structure of TNFα given above, it is recalled that the biologically active TNFα is a trimer of three subunits. Due to the "edge-to-face" packing the "back β-sheet" represents the "hidden" area of contact between the subunits which is completely inaccessible to solvent. Significant substitutions in this area will almost inevitably deprive the TNFα molecule of all biological activity. On the contrary the "front β-sheet" and the connecting regions provide the accessible surface area which includes the areas interacting with the TNFα receptors. Antibodies towards these areas would therefore probably be able to interfere with receptor binding and would hence possess TNFα neutralizing properties.

A person skilled in the art who wanted to construct a detoxified and yet immunogenic TNFα molecule according to WO 95/05489 would therefore as the first choice insert the immunodominant T cell epitope in the back β-sheet of the TNFα monomer. Modifications of this area would thus most probably interrupt the biological activity of TNFα and leave the receptor-accessible front β-sheet free for interaction with antibodies. This is also consistent with the discussion of the site-directed mutagenesis in the tightly packed core of the β-sandwich discussed above.

However, surprisingly it is not so. As it will appear from the test results below, the result was quite the contrary, since substitutions comprising the B and G strands of the back β-sheet surprisingly provided TNFα analogs which were unable to induce neutralizing antibodies against TNFα. On this background the modified human TNFα molecules according to the present invention are characterized in that the substitution has been made in regions of the TNFα molecule which do not comprise the B and G strands of the back β-sheet of the molecule.

Although it has not yet been fully verified experimentally, it must be assumed that this property is common to the strands forming the back β-sheet, so that preferably the substitutions should be made in regions of the TNFα molecule which do not comprise any strand of the back β-sheet. In view of the discussion above of the functional importance of the residues 31–35 it can be assumed that the connecting loops between the individual strands the back β-sheet should preferably also be avoided.

However, it is permissible that the substitution is made in regions of the TNFα molecule which only involve a segment of the D strand of the back β-sheet.

According to a preferred embodiment of the invention substitution comprises at least a segment of the H strand of the front β-sheet and of the connecting loop to the I strand of the back β-sheet, preferably amino acids 132 to 146. According to another embodiment of the invention the substitution comprises segments of the H and I strands and the entire connecting loop, preferably amino acids 132 to 152. According to yet another presently preferred embodiment of the invention the substitution comprises a segment of the D strand of the back β-sheet, at least a segment of the E strand of the front β-sheet and the entire connecting loop, preferably amino acids 65 to 79 or 64 to 84.

According to a further embodiment of the invention the substitution comprises the entire C' and C strands of the front β-sheet and a segment of the D strand of the back β-sheet, preferably amino acids 40 to 60.

According to a still further embodiment of the invention the substitution comprises at least a segment of the E strand of the front β-sheet and of one or both of the connecting loops, preferably amino acids 76 to 90.

The inserted T cell epitope should preferably be promiscuous and known to be immunogenic in a majority of human HLA class II types. Applicable epitopes can be derived e.g. from Tetanus toxoid, preferably epitope P2 and/or P30, Panina-Bordignon et al., Eur. J. Immunol. 19:2237–42, 1989. Also epitopes derived from diphtheria toxoid may be used.

The preferred modified human TNFα molecules (TNFα analogs) as referred to above with reference to the location of the substitution are shown in the enclosed sequence listing as SEQ ID NO:8 and SEQ ID NO:16.

Other applicable TNFα analogs are listed as SEQ ID NO:4, 10, 14 and 16.

The invention also relates to truncated analogs of the above-mentioned modified TNFα analogs according to the present invention. Thus, truncated analogs of TNFα molecules containing a promiscuous and immunodominant T cell epitope and one or both flanking regions comprising at least one TNFα B cell epitope, preferably comprising at least five amino acids, would also constitute a possible TNFα vaccine according to the invention. The T cell epitope would induce the proliferation of T cells when presented to MHC class II molecules by the APC, while B cell epitope would potentially be recognized by the immunoglobulin receptors on B cells, and would subsequently be presented by MHC class I molecules on these cells. This constitutes the basis for raising an immune response towards native TNFα, harbouring the B cell epitope, according the WO 95/05489 and the present invention.

B cell epitopes could be identified in the TNFα both theoretically and experimentally. Algorithms for identification of potential linear B cell epitopes have been published, and this would form the basis of an experimentally based investigation of the nature of these potential epitopes. Antibodies raised in a heterologous system (e.g. rabbits) in response to injections of such truncated TNFα molecules comprising T cell epitopes could be analyzed for in vitro capability to bind native human TNFα, preferentially in neutralizing manner. Panels of monoclonal antibodies known to be neutralizing could be screened in vitro for capability to bind the potential B cell epitopes of TNFα. Both of these are strategies for identifying the possible and best B cell epitopes.

The invention further relates to dimers, oligomers, especially trimers or multimers of the claimed modified TNFαmolecules and isolated DNA molecules that code for the claimed modified TNFα molecules.

The isolated DNA molecules encoding the preferred TNFα analogs have the sequences listed as SEQ ID NO:7 and 15, and the DNA molecules encoding the other applicable analogs are listed as SEQ ID NO:3, 9, 13 and 15.

The invention further comprises vectors comprising the isolated DNA molecules encoding the analogs and expression vectors comprising said DNA molecules operatively linked to a suitable expression control sequence.

Another aspect of the invention is a host transformed with an expression vector for said analog.

Said host may be any of the hosts commonly used for expression, e.g. a strain of bacteria, yeast or fungi or insect, mammalian or avian cell lines.

The invention further relates to a method of producing the claimed TNFα analogs, whereby host cells transformed with an expression vector for the analog is grown under suitable conditions permitting production of the analog, and the produced analog is recovered.

If desired, the modified TNFα molecules according to the invention may be expressed as or form part of a fusion protein with a suitable adjuvant molecule, preferably an immunologically active adjuvant, such as GM-CSF, HSP70 or an interleukin, e.g. interleukin 2.

More specifically, the modified TNFα molecules are produced by substituting the appropriate gene segments encoding the immunodominant T cell epitopes into the gene encoding the native human TNFα molecule. Subsequently the modified TNFα gene is expressed in an appropriate eukaryotic or prokaryotic expression vector. The expressed modified TNFα molecules are purified and refolded as described below.

According to the invention the modified human TNFα molecules may be used in vaccines against TNFα. Usually vaccines require the use of adjuvants. According to the invention the modified human TNFα molecules can be formulated with such appropriate adjuvants, e.g. aluminium phosphate (Adju-Phos) or other alternative adjuvants such as aluminium hydroxide, calcium phosphate, muramyl dipeptide analogs, Iscom's or other known adjuvants used in mammalian vaccines.

The vaccines may be directed against any of the TNFα-dependent diseases described above, in particular chronic inflammatory diseases. As examples can be mentioned rheumatoid arthritis and inflammatory bowel diseases (IBD). The latter includes ulcerative colitis and Crohn's disease, in particular Crohn's colitis. Other examples are cancer, cachexia, often related to cancer, disseminated sclerosis, diabetes, psoriasis, osteoporosis and asthma. Preferably the vaccines will be given as a preventive treatment, but in view of the chronic nature of these diseases and their tendency to remission and recurvency, they may also be administered to patients, where one or more of the above-mentioned diseases has been diagnosed, and may serve to maintain the patient in a state of remission.

Based on earlier studies in mice, it is believed that the modified TNFα analogs according to the invention can also be administered as part of a curative treatment of the above-mentioned diseases in an acute state or at least with a view to bringing the patient in remission and maintain a steady state condition.

At present no specific effective dose range can be stated, since the vaccines have not yet been tested in human beings susceptible to any of the diseases.

At any rate the administered dose will be prescribed by the responsible doctor.

According to one embodiment of the invention the vaccine comprises a mixture of two differently modified TNFαmolecules containing two different T cell epitopes e.g. P2 and P30 which are derived from tetanus toxoid. This mixture optionally contains appropriate amounts of pharmaceutically adjuvant According to yet another aspect of the invention, the vaccines do not comprise the modified human TNFα molecules as such, but rather a construct comprising non-infectious non-integrating DNA sequence encoding said molecules operatively liked to a promoter sequence which can control the expression of said DNA sequence in humans, in an amount sufficient that uptake of said construct occurs, and sufficient expression occurs to induce a neutralizing antibody response against TNFα.

The utility of this type of vaccines, the so-called DNA vaccines, is illustrated e.g. in U.S. Pat. Nos. 5,589,466 and 5,580,859, both of which are incorporated herein by reference, in particular in relation to the methods of administration.

The DNA vaccines may comprise a viral expression vector, such as a retroviral expression vector.

Generally, the vaccines according to the invention may be adapted for oral or parenteral, in particular subcutaneous, intramuscular or intradermal administration.

The invention further comprises the use of antibodies raised by administering a vaccine according to the invention, preferably monoclonal antibodies, particularly a diagnostic use.

The invention further relates to a method of testing human body fluids for the presence of TNFα which comprises contacting a composition containing modified TNFα according to the invention with a sample of human body fluid and determine, whether said antibodies bind to TNFα in said sample.

The invention also relates to a diagnostic method for TNFα-related diseases employing an in vitro immunoassay to detect TNFα in human body fluids.

Said methods may involve the use of a sandwich assay, ELISA assay or equivalent assay, which can be unamplified or amplified, e.g. using avidin/biotin technology.

EXPERIMENTAL PART WITH DESCRIPTION OF PREFERRED EMBODIMENTS

1. Introduction

In the previous application WO 95/05489 it was shown that T cell epitope modified murine TNFα molecules could induce high titers of antibodies cross-reactive with native murine TNFα. These antibodies were able to interfere with TNFα and its receptor in vitro as well as in vivo. Beneficial effects of immunization against TNFα were demonstrated in several animal models of TNFα-induced disease such as experimental cachexia, collagen arthritis and experimental allergic encephalomyelitis (EAE). These animal experimental results were obtained despite the fact that the two modified murine TNFα molecules used (denominated MR 103 and MR 106) were not optimized to be immunogenic in the MHC class II haplotypes of DBA/1 and SJL mice. These mouse strains were used for the collagen arthritis and the EAE experiments, respectively.

MR 103 and MR 106 were mouse molecules and based on the prior application WO 95/05489 no specific conclusions could be drawn with regard to the immunogenicity of appropriately T cell substituted human modified TNFα molecules nor about the potential ability of such molecules to induce TNFα neutralizing autoantibodies.

2. Development of Human TNFα Constructs

In general terms in a TNFα vaccine for human use the modified human TNFα molecules should fulfill the following requirements:

a. They should be immunogenic in a large proportion of the population b. They should be optimally able to induce TNFα neutralizing antibodies c. They should not possess any remaining biological TNFα activity Furthermore, in a selection process other practical parameters such as levels of recombinant expression, ease of purification, solubility etc. could also be considered.

2.1. Immunological Promiscuity of the Modified TNFα Molecules

During the development of the human TNFα vaccine the aim was to produce modified human TNFα molecules which eventually will be immunogenic in the largest possible part of the human population which of course represents a large number of different HLA class II types. Therefore, instead of the MHC specific epitopes used in the previous animal experiments, promiscuous T cell epitopes were used. It was not known from the previous application WO 95/05489 how such epitopes could influence the capability of such molecules to induce neutralizing antibodies.

The two tetanus toxoid (TT) derived T cell epitopes, P2 and P30, which have been well characterized in the scientific literature were chosen. These epitopes are known to be immunodominant in TT and to be able to bind to at least 80% of the HLA class II molecules in the human population.

Furthermore, by using these TT epitopes it was expected to be possible to test the immunogenicity of the TNFα constructs in vitro on peripheral blood mononuclear cells (PBMC) and T cell lines generated from TT immune blood donors.

The amino acid sequence of the P2 epitope is QYIKNSKFIGITEL (residues 225 to 239 of SEQ ID NO: 3) and corresponds to TT amino acids 830–844, and the sequence of the P30 epitope is FNNFTVSFWLRVPKVSASHLE (residues 224 to 244 of SEQ ID NO: 15) and corresponds to TT amino acids 947–967. Substituting P2 and P30 into two different human TNFα molecules would exchange approximately 10% and 15%, respectively, of the native TNFα sequence. In case both epitopes were inserted into a single TNFα molecule, about 25% of the molecule would be exchanged, and one could fear that this would interfere too much with the remaining native parts of the TNFα molecule. It was therefore decided to develop two TNFα molecules, each containing either P2 or P30. Together, such two molecules would be expected to be immunogenic in at least 80% of the human population. In addition, it is very likely that truncated molecules composed partly of the P2 or P30 epitope and partly of TNFα flanking regions also will con-tribute to the immunogenicity resulting in the constructs being immunogenic in almost 100% of the population.

Although it was possible to induce antibodies with all murine TNFα constructs in all mouse strains tested so far, one would a priori expect, that insertion of the foreign T cell epitope at certain positions in TNFα would be more beneficial than other positions with regard to the presentation of the epitope to T cells by MHC class II molecules. It was therefore decided to produce an array of differently modified human TNFα molecules with the P2 and P30 epitope inserted at different positions in the molecule, see FIG. 4. Subsequently, all molecules were tested in vitro in T cell assays based on peripheral blood mononuclear cells (PBMC) or P2/P30 specific T cell lines isolated from a number of healthy TT immune blood donors.

Contrary to what was expected, however, it was shown that although minor quantitative differences were seen, the intramolecular position of the P2 and P30 epitopes was not essential for the ability to be processed by antigen presenting cells and subsequently presented to TT specific T cells. Thus, P2 inserted in positions 132 to 146, 65 to 79 and 76 to 90 and P30 inserted in positions 40 to 60 and 132 to 152 (TNF2-5,2-3, 2-7, 30-2, 30-5) were all processed and presented to T cells. So from the discussion above it is very likely, that these molecules eventually will be universally immunogenic in the human population.

2.2. The Ability of the Modified Human TNFα Molecules to Induce Neutralizing Antibodies As mentioned above, it was not possible from the previous mouse studies described in WO 95/05489 to predict which position would be most appropriate in order to be able to induce neutralizing TNFα antibodies. An array of different human TNFα molecules with P2 or P30 inserted at different positions was therefore produced. The substitutions were randomly distributed over the entire molecule. The antibodies induced in rabbits upon injection of these molecules were subsequently tested in biochemical as well as biological in vitro assays for their ability to interfere with TNFα biological activity.

It has been shown in non-published observations by the present inventors that depending on the intramolecular position of the inserted epitope a different overall specificity of the induced autoantibodies was observed. Quite contrary to what would be expected based on the structural data of the TNFα molecule it was observed, that substitutions in the front β-sheet with either P2 or P30 totally deprived the molecules of biological TNFα activity, but at the same time preserved the ability of the modified molecules to induce TNFα neutralizing antibodies.

The molecules containing P2 or P30, in the positions mentioned above, were shown to be particularly effective at inducing neutralizing antibodies. Any of these molecules are therefore potential candidates for use in human TNFα vaccines.

2.3 The Biological Activity of the Different TNFα Constructs

It would obviously not be feasible to use a molecule which is as toxic as TNFα in a vaccine. The modified TNFα molecules would therefore have to be non-toxic i.e. devoid of any residual TNFα activity.

All mutant TNFα proteins were therefore tested in vitro in TNFα dependent bioassays as well as receptor binding assays in order to examine whether they are non-toxic. It was shown clearly that the modified human TNFα molecules (TNF2-5 SEQ. ID. NO. 7, 2-3 SEQ. ID. NO. 3, 2-7 SEQ. ID. NO. 9, 30-2 SEQ. ID. NO. 13, and 30-5 SEQ. ID. NO. 19,) all were deprived of TNFα biological activity. So all the necessary requirements of these molecules to be part of a universally, non-toxic vaccine capable of inducing anti-human TNFα neutralizing antibodies were fulfilled Example 1

Genetic Construction Work

It was decided to produce 10 different modified human TNFα molecules—five containing the P2 and five containing the P30 epitope. The epitopes were distributed at different positions within the molecule. The genetic constructions were made by using various standard restriction enzyme and PCR based mutagenesis techniques. The genetic constructs are shown schematically in FIGS. 4a and 4b. DNA sequences encoding the modified TNFα molecules and the corresponding amino acid sequences are incorporated as SEQ ID NO:1–SEQ ID NO:20. The constructions of the mutant human TNF2-5 gene, the cloning and mutation strategy, and the subsequent expression, isolation and purification of the TNF2-5 analog is explained below by way of example.

Construction and Production of TNF2-5:

Genetic Construction of the Mutant Human TNF2-5 Gene, Cloning and Mutation Strategy.

The genetic construction of the gene encoding the mutant human TNF2-5 analog was based upon traditional PCR based mutagenesis techniques, as were all the other genetic constructions.

The native DNA sequence of human TNFα encoding the soluble part of this molecule was obtained by traditional PCR cloning using synthetically synthesized primers I and II (table 1 and SEQ ID NO:21 and 22) from a human commercially available cDNA library, CLONTECH Laboratories, Palo Alto, Calif., USA (FIG. 16, 1). The native gene was inserted into a commercial E. coli expression vector pET28c available from Novagen, Madison, Wis. 53711, USA, in such a way that the gene could be transcribed in frame from an IPTG inducible promoter.

The genetic construction of the TNFα mutant analog TNF2-5 was performed by a PCR mutagenesis technique applied to the native DNA sequence. The nucleic acid sequence encoding the T cell epitope was incorporated into a synthetically synthesized 75-mer oligonucleotide (Primer "mut2-5", table 1 and SEQ ID NO:27) between the two 3'- and 5'-annealing stretches of TNF homologous DNA, the "mut" primer is thus capable of annealing to the native human TNFα gene sequence at the defined site selected for TNF2-5, (see FIG. 16, 2a). In the "mut" oligonucleotide the number of codons encoding the T cell epitope exactly matched the number of TNF-codons omitted between the two 3'- and 5'- annealing stretches of TNF homologous DNA. The mutagenesis primer was used to produce a PCR product containing the DNA encoding the T cell epitope and the TNFα sequence below (or 3') to the inserted epitope, (FIG. 16, 2a). The stretch of TNFα DNA above (or 5') to the point of insertion of the epitope was provided by a second PCR product using primers I and III (Table 1, SEQ ID NO:23) (FIG. 16, 2b). The two PCR products are eventually joined together in a final PCR reaction, (FIG. 16, 3) using the two most distal primers, (I, II) from the two reactions. The complete mutant TNF2-5 DNA sequence is then introduced into a commercial E. coli expression vector in analogy to the expression cloning of the native gene in such a way that the gene could be transcribed from an IPTG inducible promoter from transformed cells.

The "mut" primers used for construction of the other analogs (TNF2-1,2-3, 2-4,2-7, 30-1, 30-2, 30-3, 30-4 and 30-5) are identified as SEQ ID NO:23–26 and 28–33, respectively.

TABLE 1

Primer I SEQ. ID. NO. 21  HumanTNF-alpha FW.  24'-mer.
    Ncol-site
5'-GAC AAG CCC ATG GTC AGA TCA TCT-3'
Primer II SEQ. ID. NO. 22  HumanTNF-alpha Rev  30'-mer.
    Xbal-site.
5'-TCT CTA GAG GGC AAT GAT CCC AAA GTA GAC-3'
Primer "mut2–5" SEQ. ID.  Mutant oligo"P2–5 (tt830–44),  75'-mer.
NO. 27
5'-G AAG GGT GAC CGA CAG TAC ATT AAG GCC AAT TCG AAG TTC ATT GGC ATC ACT GAG CTG TCT GGG CAG GTC TAC TT-3'
Primer III SEQ. ID. NO. 23  HumanTNF-alpha Rev 2'nd.  21'-mer.
5'-CCC AAA GTA GAC CTG CCC AGA-3'

Cultivation of Recombinant Bacteria, Harvest and Dissolve Inclusion Bodies.

Protein Purification of the TNF2-5 Analog

The production of the TNF2-5 protein was analogous to the production of the other recombinant TNF molecules.

1. Inoculate 20 ml TB medium containing 50 μg/ml Carbenicillin with the transformed *E. coli* strain carrying the IPTG inducible plasmid vector harbouring the TNF gene encoding the recombinant protein, grow the *E. coli* over night at 37° C. with shaking.

2. Dilute the over night culture 1:25 in 250 ml TB medium with 50 μg/ml Carbenicillin, and grow the culture until $OD_{450}$ is 1. Induce the expression of the recombinant protein by adding IPTG to a final concentration of 1 mM. Grow over night with vigorous shaking at 37° C.

3. Harvest the recombinant cells from the medium by centrifugation at 3500×g. Wash the pellet once in BSB buffer. Use 150 ml BSB per 50 g wet weight bacteria.

4. Sonicate 4 times 30 seconds at maximal amplitude until the bacterial suspension is completely homogeneous. The sonication is performed using a MSE Soniprep 150 sonicator mounted with a 9.5 mm standard probe (Soniprep 05 38 121–1154)

5. Add 8 μl PMSF (50 mM) and 80 μl lysosyme solution (10 mg/ml) per gram of cell pellet. Incubate 30 min at RT 6. Add 4 mg deoxycholic acid per gram pellet, mix and store at 37° C.

7. When the solution has become viscous add 20 μl DNAse (1 mg/ml) per gram pellet and $MgCl_2$ to a final conc. of 5 mM, mix and store at room temperature for 30 min.

8. Sonicate in ice 5 times 30 seconds with 30 seconds intervals at maximum amplitude, until the solution has become fluid and non-viscous.

9. Centrifuge at 20.000×g for one hour, preserve the supernatant for later checking of the washing procedure to check if all the inclusion bodies have been precipitated.

10. Resuspend the pellet in MiliQ water (1 ml $H_2O$ per gram of *E. coli*), shake 1 hour.

11. Centrifuge at 20.000×g for one hour, preserve the supernatant to check if all the inclusion bodies have been precipitated.

12. Resuspend the pellet in 1 M urea dissolve in 1 ml per gram of *E. coli*, shake 1 hour.

13 Centrifuge at 20.000×g for one hour, preserve the supernatant to check if all the inclusion bodies have been precipitated.

14 Resuspend the pellet in 1 M guanidine dissolved in 1 ml per gram of *E. coli*, shake 1 hour.

Centrifuge at 20.000×g for one hour, preserve the supernatant to check if all the inclusion bodies have been precipitated.

16 Resuspend the pellet in 25 ml 6 M guanidine +20 mM Tris pH 8.0, agitate over night.

17 Centrifuge at 20.000×g for one hour, preserve the supernatant containing the recombinant protein inclusion bodies, preserve the pellet to check if all the inclusion bodies have been dissolved 18 The protein solution is extensively dialyzed against MilliQ water, and subsequently the solution is freeze dried.

19 The freeze dried material is solubilized in 20 mM Tris, 6 M guanidine, 30% 2-propanol (pH 8.0) at a concentration of 20 mg/ml. It is allowed to solubilize overnight under gentle agitation. The presence of monomers is examined on a superdex 200 column (XK 16, Pharmacia, diameter: 1.6 cm, height: 750 cm.). Run in running buffer at 1 ml/min. Compared to standards in the same buffer.

20 Protein purification is performed by gel filtration on a superdex 200 column (XK26, Pharmacia; height: 100 cm, diameter: 2.6 cm) which is equilibrated with equilibration buffer. Run in the equilibration buffer. A sample volume of about 1% of total column volume is applied.

21 Refolding of the recombinant protein is performed by dialysis. The protein is diluted to 0.1 mg/ml in equilibration buffer, and this solution is placed in a boiled dialysis bag and dialyzed against: 20 mM Tris, 4 M urea (pH 8.5) with three changes, one night over at room temperature. The dialysis bag is transferred to a Tris buffer (20 mM Tris, 150 mM NaCl (pH 8.0)). Change three times of which the first one takes place at room temperature. Overnight in the cold room.

Refolding is evaluated on a Superose 12 column equilibrated in Tris buffer (20 mM Tris, 150 mM NaCl (pH 8.0)). Compare to standards.

Storage. The recombinant proteins are stored freeze dried.

TB Medium

Dissolve Terrific Broth (GIBCO BRL 22711–22) in MiliQ water according to the manufacturers instruction. Autoclave at 121° C. for 20 min.

Carbenicillin×100 Stock Solution (50 mg/ml)

Carbenicillin disodium salt (Sigma C1389) is dissolved in MiliQ water at a concentration of 50 mg/ml. The solution is filtersterilized through a 0.2 μm filter (Sterifix 0409 9206)

IPTG×100 Stock Solution 100 mM

Isopropyl-beta-D-thiogalactopyranoside (IPTG, USB 17884) 1.19 g IPTG is dissolved in MiliQ water ad 50 ml. The solution is filtersterilized through a 0.2 μm filter (Sterifix 0409 9206)

BSB Buffer

Bacterial Suspension Buffer 50 mM TRIS (Trisma base, SigmaT1503)

0.5 M NaCl (Ridel-de.Haën 31434)

5 mM DTT (DL-dithiothretiol, Sigma D-0632)

pH 8.0

PMSF 50 mM, phenylmethylsulfonylfluride, SIGMA # P-7626, dissolved in 2-propanol Lysosyme Solution 10 mg/ml Grade III lysozyme from chicken egg white, (EC 3.2.1.17) SIGMA # L-7001

Deoxycholic Acid (7-deoxycholic acid) Sigma # D-6750

DNAse 1 mg/ml Dnase I, Deoxyribonuclease I, (EC.3.1.21.1) Boehringer Cat # 1284932

UREA

Urea (GibcoBRL 15716-020)

Guanidine

Guanidine hydrochloride (Sigma G4505)

2-Propanol

Running Buffer 20 mM TRIS, (Trisma base, SigmaT1503)

8 M urea, (GibcoBRL 15716-020)

0.1% β-mercaptoethanol pH 8.0

Equilibration Buffer 20 mM TRIS, (Trisma base, SigmaT1503)

8 m urea, (GibcoBRL 15716-020)

0.1% β-mercaptoethanol

Example 2

Expression, Purification and Refolding of P2 and P30 Modified TNFα Molecules

It is well established that recombinant proteins behave differently during expression, purification and refolding. All proteins were expressed in *E. coli* and expression levels ranging from 2-20% were obtained. All tee proteins were recognized in Western blotting experiments using a commercially available polyclonal rabbit-anti human TNFα antibody.

The TNFα constructs were subsequently expressed one by one in 250 ml cultures in batch sizes of 3-4 l. All modified TNFα proteins were expressed as inclusion bodies and more than 85% pure and refolded protein preparations were produced as described above.

The protein content was determined with standard BCA analysis. All protein purifications were performed in at least three separate runs for each molecule, and in all cases the separate protein batches were tested and found similar. The proteins were stored in concentrations from 0.2–1.0 mg/ml in PBS at −20° C. until use.

Standard quality control analyses included SDS gel electrophoresis with both Coomassie blue staining and silver staining of the individual protein preparations. In all cases the proteins were found to be of the expected size and to be more than 85% pure.

Molecules with epitopes inserted at position 4 (TNF2-4 and TNF30-4) were only expressed at relatively low levels (app. 2%). These molecules were furthermore very difficult to purify and especially their refolding was troublesome. Both molecules, but in particular TNF30-4, were not very soluble in PBS and tended to precipitate during storage.

Example 3

Biological Activity of the Different TNFα Constructs

The direct biological activity of the purified TNFα molecules was tested in the L929 bioassay which is a standard in vitro assay for determination of biological TNFα activity. As seen in FIG. 6 none of the P2 or P30 modified TNFα molecules were able to kill L929 cells in the concentration range tested (up to 60 mg/ml). A commercially available recombinant TNFα molecule were fully active at about 0.6 ng/ml. The wild type TNFα preparation was also fully active in the entire concentration range tested.

Example 4

The Ability of the Modified TNFα Molecules to Induce Neutralizing Antibodies

Rabbits were immunized with each of the ten constructs to see whether these were able to induce antibodies capable of neutralizing biologically active human TNFα in vitro. Groups of three rabbits were used and each rabbit received 100 mg TNFα s.c. in Freunds Complete Adjuvant and subsequently 100 mg approximately every third week in Freunds Incomplete Adjuvant.

During the entire immunization period of 18 weeks blood samples were collected at regular intervals and the sera were tested for anti-TNFα activity in a conventional ELISA assay where commercially available, pure and non-modified human TNFα was used as the antigen.

All rabbits developed anti-TNFα antibodies during the immunization period and the maximum level or antibody titers varied within a decade within each group. The average antibody titers are shown in FIG. 7. TNF2-5, TNF2-7, TNF2-3, TNF2-1 and WT-TNFα induced a titer of one hundred within 2-4 weeks whereas TNF2-4 gave a remarkably slower response. Similar kinetics were observed for the TNF30 proteins where a slower response also was obtained with TNF30-4.

The ability of these sera to interfere with human TNFα and its receptor was tested in the L929 assay as well as in a solid phase receptor binding assay.

In the L929 assay dilutions of immune sera as well as a non-immune control serum were added to commercially available human TNFα prior to the addition of the mixture to L929 cells. Sera from all three rabbits in each group were tested in duplicates and the average values were calculated. Since normal serum tended to increase the background values of the color detecting system these were subtracted from all values and the relative inhibition in percent was calculated. The results for the inhibitory capacity at week 14 in the immunization schedule of all rabbits are shown in FIG. 8.

TNF2-5 which does not comprise substitutions in any segment of the back β-sheet strands is clearly superior compared to the other constructs and this molecule was comparable to the fully toxic WT-TNFα molecule with regard to the ability to induce neutralizing antibodies (data not shown). TNF2-3 which comprises a small substituted segment in the D β-strand and TNF2-7 which does not comprise any substituted segment of the back β-sheet strands, were also able to induce inhibitory antibodies, and the neutralizing antibody titer towards TNF2-7 increased significantly during the following three weeks (data not shown). TNF2-4 and TNF2-1, which comprise the G and B β-strands, respectively, of the back β-sheet, were unable to induce neutralizing antibodies in the L 929 assay.

The results with regard to the TNF30 proteins were more heterogeneous although TNF30-3 seemed to be best at week 14. TNF30-1 and TNF30-4, which comprise substitutions in the G and B β-strands of the back β-sheet, respectively, did not induce neutralizing antibodies in the L929 assay.

In the solid phase receptor binding assay recombinant human 55 kD TNFα receptor 1 (TNF-R55) was immobilized on microtiter plates and commercially available biotinylated human TNFα was added in an appropriate dilution. Specific binding to the receptor was subsequently detected with horse radish peroxidase labeled streptavidin and a chromogenic substrate. When testing sera from immunized rabbits these were added to the biotinylated human TNFα solution prior to the addition of the mixture to the TNF-R55 coated microtiter plate. Sera from all three rabbits in each group were tested and the average values were calculated. Serum from a non-immunized rabbit was used as negative control. The background values were very low and the assay is highly sensitive. The results are shown in FIG. 9.

It can be seen that the results obtained from the L929 assay and the solid phase receptor binding assay, respectively, are almost identical with regard to the TNFα2 constructs. In the solid phase assay the difference between TNF30-2, 30-3 and 30-5 was not as pronounced as observed in the L929 assay. The solid phase assay is, however, more reproducible due to its biochemical rather than cellular character, and normal serum values were not subtracted in this assay.

The relative amounts of serum (in percent) by which half maximum inhibition of TNFα binding was achieved (IC values) were calculated for TNF2-3, TNF2-5, TNF2-7, TNF30-2, TNF30-3, TNF30-5 and WT-TNFα for each of the corresponding antisera. Assuming that a similar curve shape would appear for antisera raised against TNF2-1, TNF2-1, TNF30-1 and TNF30-4 extrapolations were performed, and IC50 values were also calculated for these sera. The results are shown in Table II.

TABLE II

IC50 values of rabbit-anti human TNFα sera in the solid phase assay

| 2-1 | 2-3 | 2-4 | 2-5 | 2-7 | WT | 30-1 | 30-2 | 30-3 | 30-4 | 30-5 |
|---|---|---|---|---|---|---|---|---|---|---|
| >100% | 2.02% | >100% | 0.53% | 1.38% | 0.43% | >100% | 0.82% | 0.88% | >74% | 1.69% |

It can be seen that TNF2-5 is equivalent to wild type (WT) mouse TNFα with regard to the ability to induce neutralizing anti-mouse TNFα antibodies in rabbits. TNF2-1, TNF2-4, TNF30-1 and TNF30-4 which all comprise substitutions in the B or G strand of the back β-sheet are very poor or even totally unable to induce such antibodies.

This indicates surprisingly that although the strands B and G of the back β-sheet are not involved in receptor binding, the mutations represented in this area anyhow lead to disturbance of the regions of human TNFα involved in receptor binding. TNF30-2 and TNF30-3 seem to induce neutralizing antibodies equally well.

Example 5

The Ability of the Modified TNFα Molecules to Stimulate T Cells from P2 and P30 Immune Healthy Blood Donors Since it was expected that the localization of the P2 and P30 epitopes in the modified TNFα molecules also would affect the antigen processing and presentation of the inserted epitopes—and thus their immunogenicity—all 10 molecules were tested in different T cell assays. A polyclonal Peripheral Blood Molecular Cell (PBMC) assay was used, and a number of P2 and P30 specific T cell lines were established using conventional immunological methods to test TNFα peptides and recombinant proteins with inserted P2 and P30 epitopes.

Initially 28 healthy volunteers (donors) were tested in a conventional PBMC proliferation assay for their ability to respond to TT and the P2 and P30 peptides. On the basis of these results 19 individuals capable of responding significantly to TT, P2 as well as P30 peptides were selected for further experiments. Although the response levels varied much, this clearly confirmed that P2 and P30 are promiscuous as well as immunodominant T cell epitopes.

In addition to the 28 donors, seven further donors were also selected. For reasons explained below some of these were selected for their ability to respond either to P30 or to P2. Several of these were furthermore vaccinated with TT in order to be able to give a strong T cell response. Some of the second group of donors were also used to raise P2 or P30 specific T cell lines in order to study the antigen presentation of P2 and P30 modified synthetic TNFα peptides as well as the modified molecules. In FIG. 10 representative examples of the polyclonal PBMC proliferative response in three donors towards TT as well as the P2 and P30 peptides are shown.

All 10 recombinant proteins were tested in triplicate in at least 6 different concentrations starting from about 100 mg/ml, and all PBMC experiments were repeated 2-3 times for each individual. Intracellular incorporation of $^3$H-labelled thymidine was used to assess T cell proliferation, and the experiments were harvested and counted in a 96-well format. The maximum proliferation indexes (PI) from each titration curve was calculated as the relation between the average number of CPMs in the experimental wells divided by the average number of CPMs obtained in the antigen free wells (PBS only). The T cell proliferation data were made in triplicate and Con A as well at the P2 and P30 were used as negative and positive controls, respectively. In FIG. 11 three examples are shown from experiments with two different blood donors using the different P2 and P30 modified TNFα molecules.

JH only responds to P2, whereas SR responds to both P2 and P30. This is also reflected in the proliferative responses to the P2 and P30 modified TNFα proteins which to a varying extent almost all are able to stimulate the PBMCs.

In FIG. 12 the Proliferation Indexes (PIs) calculated from 34 experiments are shown. Although it is very difficult to quantitatively compare PIs between different experiments due to varying PBS backgrounds it seems clear that all constructs more or less are capable of eliciting a proliferative response.

Among the second group of donors some individuals were vaccinated against TT 1-2 months before the experiments. The PIs obtained from these persons (HB, MR, KG, and MW) were all among the highest PIs observed for all the modified TNFα constructs and the data were easy to evaluate. Three other individuals (DL, ID, and LS) were vaccinated more than 5 years back, and they all showed PI values below average. This supports that the observed PIs were antigen specific. No data regarding the last TT vaccination dates were available for the first group of donors, but their immunization status was clearly very variable.

It is not possible to select a preferred TNFα 2 or TNFα 30 protein merely based on the average size of the PI values. This may be due to the heterogeneous vaccination status of the individual used and the variable nature of PBMC assays obtained from individuals with variable responder status. It was anyway surprising, that P2 and P30 at all the inserted positions in TNFα seemed to be able to be processed and presented to T cells. In order to exclude the possibility that despite repeated affinity chromatography, gelfiltration and dialysis, the antigen preparations could still contain significant concentrations of non-specific mitogens, some further experiments were performed.

Donors from the second group known to be non-responders to P2 and responders to P30 as well as donors with the opposite response pattern were tested in PBMC assays. In FIG. 13 the response to P2, P30 as well as the TNFα2 and TNFα 30 proteins are shown for DL and ID.

It can be seen that specific responses are obtained to the respective T cell epitopes and the respectively modified TNFα molecules. However, no significant proliferative responses of DL against TNFα 30 proteins were observed (upper panel) and no significant proliferative responses of ID to TNFα 2 proteins were observed (lower panel) supporting that non-specific mitogens were absent in the purified TNFα preparations.

This possibility was even further examined by the use of P2 and P30 specific T cell lines isolated from the second group of donors, which had been cultured for at least six weeks in at least three rounds of stimulation with the respective synthetic P2 and P30 peptides. In FIG. 14 the results of two such experiments are shown.

It can be seen that the P2 and P30 specific T cell lines were only stimulated by their corresponding P2 and P30 proteins. Furthermore, it can be seen again that all TNFαconstructs are able to induce T cell proliferation emphasizing that although antigen processing may be quantitatively important for presentation of P2 and P30, it does not seem to be a significant qualitative limiting factor for antigen presentation.

It has been reported in the literature that flanking regions of T cell epitopes can influence the binding of antigenic peptides to MHC class II molecules. Since none of the positions in TNFα, which were chosen for insertion of P2 or P30, seemed to be prohibitive for antigen presentation, it was investigated whether the different flanking TNFα sequences of the inserted epitopes could influence the T cell response to P2 and P30 epitopes as a result of differential binding to the human HLA class II molecules. The peptides shown in Table III, which represent the inserted epitopes as well as the flanking human TNFα amino acids were therefore synthesized. These are designated PP2-5, PP30-3, etc. The amino acid sequences are shown in the sequence listing as SEQ ID NO:34 to SEQ ID NO:42 designated Pep2-1 to Pep30-5.

good potential antigen and these data further supports that the observed T cell proliferations are antigen specific. There was generally no qualitative differences in the stimulation pattern when the P30 specific T cell lines from MR and KG were stimulated either with peptides or proteins (data not shown). The P30 specific T cell line from HC preferably recognized with TNF30-3 and reacted to a minor extent with TNF30-2.

CONCLUSION

Ten differently modified human TNFα proteins have been produced and characterized. They were constructed to contain two well known promiscuous T cell epitopes P2 and P30 in order to be potentially immunogenic in at least 85% of the populations.

All proteins could be expressed and purified although TNF2-4 and TNF30-4 at low levels. Mutations at this position in TNFα also seems to interfere with refolding which results in proteins with poor solubility. No biological TNFα activity could be detected in any of the modified TNFα molecules.

Rabbits were immunized with all ten proteins as well as with native TNFα. After 2-3 months of immunization it was possible to detect high titers of strongly cross-reactive antibodies towards human, non-modified TNFα in all sera.

The ability of these antibodies to interfere with the biological activity of native TNFα was tested in two different in vitro assays—the L929 bioassay and a solid phase receptor binding assay. Both assays showed essentially the same TNF2-1, TNF2-4, TNF30-1 and TNF30-4 was not able to induce significant neutralizing antibodies, whereas TNF2-5 was superior compared to the other constructs. TNF30-2 and TNF30-3 were equally efficient at inducing neutralizing antibodies and twice as good as TNF30-5 which was reasonably good.

Somewhat surprisingly it was not possible to see significant differences between the abilities of the molecules to stimulate PBMC to proliferate. It could be demonstrated that this was not due to the presence of mitogens in the antigen preparations and based on these data, it was concluded that the locations chosen for P2 and P30 all allowed presentation of the respective epitopes. The specificity of the responses was further documented by using testing the modified TNFα

TABLE III

Synthetic peptides representing P2 and P30 and their flanking TNFα regions

| | |
|---|---|
| 2-1 SRTPSQYIKANSKFIGITELQLQWL | 30-1 SRTPSFNNFTVSFWLRVPKVSASHLERRANA |
| 2-3 SQVLFQYIKANSKFIGITELISRIA | 30-2 ALLANFNNFTVSFWLRVPKVSASHLEQVLFK |
| 2-4 AEAKPQYIKANSKFIGITELGDRLS | 30-3 YSQVLFNNFTVSFWLRVPKVSASHLEVSYQT |
| 2-5 EKGDRQYIKANSKFIGITELSGQVY | 30-4 QRETPFNNFTVSFWLRVPKVSASHLEKGDRL |
| 2-7 ND | 30-5 EKGDRFNNFTVSFWLRVPKVSASHLEGIIAL |

These peptides were used for stimulation of P2 and P30 specific T cell lines. The results from stimulation of the P30 lines are shown in FIG. 15. It can be seen that the P2 specific T cell lines from MR and KG shows parallel stimulation patterns when stimulated either with the peptide or with the corresponding TNFα2 protein. It is clear that TNF2-5 is a proteins using epitope specific T cell lines as well as synthetic peptides representing the inserted epitopes as well as the flanking TNFα sequences. From these experiments it was clearly demonstrated that TNF2-5, TNF30-2 and TNF30-3 (among other constructs) were the most powerful potential immunogens.

SEQUENCE LISTING (1) GENERAL INFORMATION:

(iii) NUMBER OF SEQUENCES: 44

(2) INFORMATION FOR SEQ ID NO: 1:

(i) SEQUENCE CHARACTERISTICS:
       (A) LENGTH: 474 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (iv) ANTI-SENSE: NO (vi) ORIGINAL SOURCE:
       (A) ORGANISM: Homo sapiens (ix) FEATURE:
       (A) NAME/KEY: CDS
       (B) LOCATION:1..474
       (C) IDENTIFICATION METHOD: experimental
       (D) OTHER INFORMATION:/codon_start= 1
           /function= "Antigen"
           /product= "TNF-alpha analog"
           /evidence= EXPERIMENTAL
           /gene= "tnfP2-1"
           /standard_name= "TNF2-1"

(xi) SEQUENCE DESCRIPTION: SEQ ID NO: 1:

```
ATG GTC AGA TCA TCT TCT CGA ACC CCG AGT CAG TAC ATT AAA GCC AAT         48
Met Val Arg Ser Ser Ser Arg Thr Pro Ser Gln Tyr Ile Lys Ala Asn
 1               5                  10                  15

TCT AAA TTC ATC GGT ATA ACT GAG CTG CAG CTC CAG TGG CTG AAC CGC         96
Ser Lys Phe Ile Gly Ile Thr Glu Leu Gln Leu Gln Trp Leu Asn Arg
             20                  25                  30

CGG GCC AAT GCC CTC CTG GCC AAT GGC GTG GAG CTG AGA GAT AAC CAG        144
Arg Ala Asn Ala Leu Leu Ala Asn Gly Val Glu Leu Arg Asp Asn Gln
         35                  40                  45

CTG GTG GTG CCA TCA GAG GGC CTG TAC CTC ATC TAC TCC CAG GTC CTC        192
Leu Val Val Pro Ser Glu Gly Leu Tyr Leu Ile Tyr Ser Gln Val Leu
     50                  55                  60

TTC AAG GGC CAA GGC TGC CCC TCC ACC CAT GTG CTC CTC ACC CAC ACC        240
Phe Lys Gly Gln Gly Cys Pro Ser Thr His Val Leu Leu Thr His Thr
 65                  70                  75                  80

ATC AGC CGC ATC GCC GTC TCC TAC CAG ACC AAG GTC AAC CTC CTC TCT        288
Ile Ser Arg Ile Ala Val Ser Tyr Gln Thr Lys Val Asn Leu Leu Ser
                 85                  90                  95

GCC ATC AAG AGC CCC TGC CAG AGG GAG ACC CCA GAG GGG GCT GAG GCC        336
Ala Ile Lys Ser Pro Cys Gln Arg Glu Thr Pro Glu Gly Ala Glu Ala
             100                 105                 110

AAG CCC TGG TAT GAG CCC ATC TAT CTG GGA GGG GTC TTC CAG CTG GAG        384
Lys Pro Trp Tyr Glu Pro Ile Tyr Leu Gly Gly Val Phe Gln Leu Glu
         115                 120                 125

AAG GGT GAC CGA CTC AGC GCT GAG ATC AAT CGG CCC GAC TAT CTC GAC        432
Lys Gly Asp Arg Leu Ser Ala Glu Ile Asn Arg Pro Asp Tyr Leu Asp
     130                 135                 140

TTT GCC GAG TCT GGG CAG GTC TAC TTT GGG ATC ATT GCC CTC                474
Phe Ala Glu Ser Gly Gln Val Tyr Phe Gly Ile Ile Ala Leu
145                 150                 155
```

(2) INFORMATION FOR SEQ ID NO: 2:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Val Arg Ser Ser Ser Arg Thr Pro Ser Gln Tyr Ile Lys Ala Asn
 1               5                  10                  15

Ser Lys Phe Ile Gly Ile Thr Glu Leu Gln Leu Gln Trp Leu Asn Arg
             20                  25                  30

Arg Ala Asn Ala Leu Leu Ala Asn Gly Val Glu Leu Arg Asp Asn Gln
         35                  40                  45

Leu Val Val Pro Ser Glu Gly Leu Tyr Leu Ile Tyr Ser Gln Val Leu
     50                  55                  60

Phe Lys Gly Gln Gly Cys Pro Ser Thr His Val Leu Leu Thr His Thr
 65                  70                  75                  80

Ile Ser Arg Ile Ala Val Ser Tyr Gln Thr Lys Val Asn Leu Leu Ser
                 85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
130                 135                 140

Phe Ala Glu Ser Gly Gln Val Tyr Phe Gly Ile Ile Ala Leu
145                 150                 155
```

(2) INFORMATION FOR SEQ ID NO: 3:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION:1..474
        (D) OTHER INFORMATION:/codon_start= 1
            /function= "Antigen"
            /product= "TNF-alpha analog"
            /gene= "tnfP2-3"
            /standard_name= "TNF2-3"

(xi) SEQUENCE DESCRIPTION: SEQ ID NO: 3:

```
ATG GTC AGA TCA TCT TCT CGA ACC CCG AGT GAC AAG CCT GTA GCC CAT    48
Met Val Arg Ser Ser Ser Arg Thr Pro Ser Asp Lys Pro Val Ala His
160                 165                 170                 175

GTT GTA GCA AAC CCT CAA GCT GAG GGG CAG CTC CAG TGG CTG AAC CGC    96
Val Val Ala Asn Pro Gln Ala Glu Gly Gln Leu Gln Trp Leu Asn Arg
            180                 185                 190

CGG GCC AAT GCC CTC CTG GCC AAT GGC GTG GAG CTG AGA GAT AAC CAG   144
```

```
Arg Ala Asn Ala Leu Leu Ala Asn Gly Val Glu Leu Arg Asp Asn Gln
            195                 200                 205

CTG GTG GTG CCA TCA GAG GGC CTG TAC CTC ATC TAC TCC CAG GTC CTC         192
Leu Val Val Pro Ser Glu Gly Leu Tyr Leu Ile Tyr Ser Gln Val Leu
            210                 215                 220

TTC CAG TAC ATA AAG GCC AAC TCC AAG TTT ATC GGC ATC ACC GAG CTC         240
Phe Gln Tyr Ile Lys Ala Asn Ser Lys Phe Ile Gly Ile Thr Glu Leu
        225                 230                 235

ATC AGC CGC ATC GCC GTC TCC TAC CAG ACC AAG GTC AAC CTC CTC TCT         288
Ile Ser Arg Ile Ala Val Ser Tyr Gln Thr Lys Val Asn Leu Leu Ser
240                 245                 250                 255

GCC ATC AAG AGC CCC TGC CAG AGG GAG ACC CCA GAG GGG GCT GAG GCC         336
Ala Ile Lys Ser Pro Cys Gln Arg Glu Thr Pro Glu Gly Ala Glu Ala
            260                 265                 270

AAG CCC TGG TAT GAG CCC ATC TAT CTG GGA GGG GTC TTC CAG CTG GAG         384
Lys Pro Trp Tyr Glu Pro Ile Tyr Leu Gly Gly Val Phe Gln Leu Glu
            275                 280                 285

AAG GGT GAC CGA CTC AGC GCT GAG ATC AAT CGG CCC GAC TAT CTC GAC         432
Lys Gly Asp Arg Leu Ser Ala Glu Ile Asn Arg Pro Asp Tyr Leu Asp
        290                 295                 300

TTT GCC GAG TCT GGG CAG GTC TAC TTT GGG ATC ATT GCC CTC                 474
Phe Ala Glu Ser Gly Gln Val Tyr Phe Gly Ile Ile Ala Leu
305                 310                 315

(2) INFORMATION FOR SEQ ID NO: 4:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 4:

Met Val Arg Ser Ser Ser Arg Thr Pro Ser Asp Lys Pro Val Ala His
 1               5                  10                  15

Val Val Ala Asn Pro Gln Ala Glu Gly Gln Leu Gln Trp Leu Asn Arg
                20                  25                  30

Arg Ala Asn Ala Leu Leu Ala Asn Gly Val Glu Leu Arg Asp Asn Gln
            35                  40                  45

Leu Val Val Pro Ser Glu Gly Leu Tyr Leu Ile Tyr Ser Gln Val Leu
        50                  55                  60

Phe Gln Tyr Ile Lys Ala Asn Ser Lys Phe Ile Gly Ile Thr Glu Leu
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155

(2) INFORMATION FOR SEQ ID NO: 5:

(i) SEQUENCE CHARACTERISTICS:
        (A) LENGTH: 474 base pairs
        (B) TYPE: nucleic acid
```

(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (ix) FEATURE:
    (A) NAME/KEY: CDS
    (B) LOCATION:1..474
    (D) OTHER INFORMATION:/codon_start= 1
        /function= "Antigen"
        /product= "TNF-alpha analog"
        /gene= "tnfP2-4"
        /standard_name= "TNF2-4"

(xi) SEQUENCE DESCRIPTION: SEQ ID NO: 5:

```
ATG GTC AGA TCA TCT TCT CGA ACC CCG AGT GAC AAG CCT GTA GCC CAT        48
Met Val Arg Ser Ser Ser Arg Thr Pro Ser Asp Lys Pro Val Ala His
160             165                 170                 175

GTT GTA GCA AAC CCT CAA GCT GAG GGG CAG CTC CAG TGG CTG AAC CGC        96
Val Val Ala Asn Pro Gln Ala Glu Gly Gln Leu Gln Trp Leu Asn Arg
            180                 185                 190

CGG GCC AAT GCC CTC CTG GCC AAT GGC GTG GAG CTG AGA GAT AAC CAG       144
Arg Ala Asn Ala Leu Leu Ala Asn Gly Val Glu Leu Arg Asp Asn Gln
        195                 200                 205

CTG GTG GTG CCA TCA GAG GGC CTG TAC CTC ATC TAC TCC CAG GTC CTC       192
Leu Val Val Pro Ser Glu Gly Leu Tyr Leu Ile Tyr Ser Gln Val Leu
    210                 215                 220

TTC AAG GGC CAA GGC TGC CCC TCC ACC CAT GTG CTC CTC ACC CAC ACC       240
Phe Lys Gly Gln Gly Cys Pro Ser Thr His Val Leu Leu Thr His Thr
225                 230                 235

ATC AGC CGC ATC GCC GTC TCC TAC CAG ACC AAG GTC AAC CTC CTC TCT       288
Ile Ser Arg Ile Ala Val Ser Tyr Gln Thr Lys Val Asn Leu Leu Ser
240                 245                 250                 255

GCC ATC AAG AGC CCC TGC CAG AGG GAG ACC CCA GAG GGG GCT GAG GCC       336
Ala Ile Lys Ser Pro Cys Gln Arg Glu Thr Pro Glu Gly Ala Glu Ala
                260                 265                 270

AAG CCC CAG TAT ATC AAG GCC AAT TCG AAA TTC ATC GGC ATC ACG GAG       384
Lys Pro Gln Tyr Ile Lys Ala Asn Ser Lys Phe Ile Gly Ile Thr Glu
            275                 280                 285

CTC GGT GAC CGA CTC AGC GCT GAG ATC AAT CGG CCC GAC TAT CTC GAC       432
Leu Gly Asp Arg Leu Ser Ala Glu Ile Asn Arg Pro Asp Tyr Leu Asp
        290                 295                 300

TTT GCC GAG TCT GGG CAG GTC TAC TTT GGG ATC ATT GCC CTC                474
Phe Ala Glu Ser Gly Gln Val Tyr Phe Gly Ile Ile Ala Leu
    305                 310                 315
```

(2) INFORMATION FOR SEQ ID NO: 6:

(i) SEQUENCE CHARACTERISTICS:
       (A) LENGTH: 158 amino acids
       (B) TYPE: amino acid
       (D) TOPOLOGY: linear (ii) MOLECULE TYPE: protein (xi) SEQUENCE DESCRIPTION: SEQ ID NO: 6:

```
Met Val Arg Ser Ser Ser Arg Thr Pro Ser Asp Lys Pro Val Ala His
1               5                   10                  15

Val Val Ala Asn Pro Gln Ala Glu Gly Gln Leu Gln Trp Leu Asn Arg
```

```
                     20                  25                  30
Arg Ala Asn Ala Leu Leu Ala Asn Gly Val Glu Leu Arg Asp Asn Gln
            35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Gln Tyr Ile Lys Ala Asn Ser Lys Phe Ile Gly Ile Thr Glu
        115                 120                 125

Leu Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155
```

(2) INFORMATION FOR SEQ ID NO: 7:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION:1..474
        (D) OTHER INFORMATION:/function= "Antigen"
           /product= "TNF-alpha analog"
           /gene= "tnfP2-5"
           /standard_name= "TNF2-5"

(xi) SEQUENCE DESCRIPTION: SEQ ID NO: 7:

```
ATG GTC AGA TCA TCT TCT CGA ACC CCG AGT GAC AAG CCT GTA GCC CAT      48
Met Val Arg Ser Ser Ser Arg Thr Pro Ser Asp Lys Pro Val Ala His
160                 165                 170                 175

GTT GTA GCA AAC CCT CAA GCT GAG GGG CAG CTC CAG TGG CTG AAC CGC      96
Val Val Ala Asn Pro Gln Ala Glu Gly Gln Leu Gln Trp Leu Asn Arg
            180                 185                 190

CGG GCC AAT GCC CTC CTG GCC AAT GGC GTG GAG CTG AGA GAT AAC CAG     144
Arg Ala Asn Ala Leu Leu Ala Asn Gly Val Glu Leu Arg Asp Asn Gln
        195                 200                 205

CTG GTG GTG CCA TCA GAG GGC CTG TAC CTC ATC TAC TCC CAG GTC CTC     192
Leu Val Val Pro Ser Glu Gly Leu Tyr Leu Ile Tyr Ser Gln Val Leu
    210                 215                 220

TTC AAG GGC CAA GGC TGC CCC TCC ACC CAT GTG CTC CTC ACC CAC ACC     240
Phe Lys Gly Gln Gly Cys Pro Ser Thr His Val Leu Leu Thr His Thr
225                 230                 235

ATC AGC CGC ATC GCC GTC TCC TAC CAG ACC AAG GTC AAC CTC CTC TCT     288
Ile Ser Arg Ile Ala Val Ser Tyr Gln Thr Lys Val Asn Leu Leu Ser
240                 245                 250                 255

GCC ATC AAG AGC CCC TGC CAG AGG GAG ACC CCA GAG GGG GCT GAG GCC     336
```

-continued

```
Ala Ile Lys Ser Pro Cys Gln Arg Glu Thr Pro Glu Gly Ala Glu Ala
            260                 265                 270

AAG CCC TGG TAT GAG CCC ATC TAT CTG GGA GGG GTC TTC CAG CTG GAG      384
Lys Pro Trp Tyr Glu Pro Ile Tyr Leu Gly Gly Val Phe Gln Leu Glu
            275                 280                 285

AAG GGT GAC CGA CAG TAC ATT AAG GCC AAT TCG AAG TTC ATT GGC ATC      432
Lys Gly Asp Arg Gln Tyr Ile Lys Ala Asn Ser Lys Phe Ile Gly Ile
            290                 295                 300

ACT GAG CTG TCT GGG CAG GTC TAC TTT GGG ATC ATT GCC CTC              474
Thr Glu Leu Ser Gly Gln Val Tyr Phe Gly Ile Ile Ala Leu
            305                 310                 315
```

(2) INFORMATION FOR SEQ ID NO: 8:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Val Arg Ser Ser Ser Arg Thr Pro Ser Asp Lys Pro Val Ala His
 1               5                  10                  15

Val Val Ala Asn Pro Gln Ala Glu Gly Gln Leu Gln Trp Leu Asn Arg
             20                  25                  30

Arg Ala Asn Ala Leu Leu Ala Asn Gly Val Glu Leu Arg Asp Asn Gln
         35                  40                  45

Leu Val Val Pro Ser Glu Gly Leu Tyr Leu Ile Tyr Ser Gln Val Leu
  50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
             85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
            115                 120                 125

Lys Gly Asp Arg Gln Tyr Ile Lys Ala Asn Ser Lys Phe Ile Gly Ile
            130                 135                 140

Thr Glu Leu Ser Gly Gln Val Tyr Phe Gly Ile Ile Ala Leu
145                 150                 155
```

(2) INFORMATION FOR SEQ ID NO: 9:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION:1..474
        (D) OTHER INFORMATION:/codon_start= 1

```
                  /function= "Antigen"
                  /product= "TNF-alpha analog"
                  /gene= "tnfP2-7"
                  /standard_name= "TNF2-7"

(xi) SEQUENCE DESCRIPTION: SEQ ID NO: 9:

ATG GTC AGA TCA TCT TCT CGA ACC CCG AGT GAC AAG CCT GTA GCC CAT       48
Met Val Arg Ser Ser Ser Arg Thr Pro Ser Asp Lys Pro Val Ala His
160         Arg         165             170             175

GTT GTA GCA AAC CCT CAA GCT GAG GGG CAG CTC CAG TGG CTG AAC CGC       96
Val Val Ala Asn Pro Gln Ala Glu Gly Gln Leu Gln Trp Leu Asn Arg
                180             185                 190

CGG GCC AAT GCC CTC CTG GCC AAT GGC GTG GAG CTG AGA GAT AAC CAG      144
Arg Ala Asn Ala Leu Leu Ala Asn Gly Val Glu Leu Arg Asp Asn Gln
            195             200             205

CTG GTG GTG CCA TCA GAG GGC CTG TAC CTC ATC TAC TCC CAG GTC CTC      192
Leu Val Val Pro Ser Glu Gly Leu Tyr Leu Ile Tyr Ser Gln Val Leu
        210             215             220

TTC AAG GGC CAA GGC TGC CCC TCC ACC CAT GTG CTC CAG TAC ATC AAA      240
Phe Lys Gly Gln Gly Cys Pro Ser Thr His Val Leu Gln Tyr Ile Lys
    225             230             235

GCT AAC TCC AAA TTC ATC GGC ATC ACC GAA CTG GTT AAC CTC CTC TCT      288
Ala Asn Ser Lys Phe Ile Gly Ile Thr Glu Leu Val Asn Leu Leu Ser
240             245             250             255

GCC ATC AAG AGC CCC TGC CAG AGG GAG ACC CCA GAG GGG GCT GAG GCC      336
Ala Ile Lys Ser Pro Cys Gln Arg Glu Thr Pro Glu Gly Ala Glu Ala
            260             265             270

AAG CCC TGG TAT GAG CCC ATC TAT CTG GGA GGG GTC TTC CAG CTG GAG      384
Lys Pro Trp Tyr Glu Pro Ile Tyr Leu Gly Gly Val Phe Gln Leu Glu
        275             280             285

AAG GGT GAC CGA CTC AGC GCT GAG ATC AAT CGG CCC GAC TAT CTC GAC      432
Lys Gly Asp Arg Leu Ser Ala Glu Ile Asn Arg Pro Asp Tyr Leu Asp
    290             295             300

TTT GCC GAG TCT GGG CAG GTC TAC TTT GGG ATC ATT GCC CTC                474
Phe Ala Glu Ser Gly Gln Val Tyr Phe Gly Ile Ile Ala Leu
305             310             315

(2) INFORMATION FOR SEQ ID NO: 10:

(i) SEQUENCE CHARACTERISTICS:
         (A) LENGTH: 158 amino acids
         (B) TYPE: amino acid
         (D) TOPOLOGY: linear (ii) MOLECULE TYPE: protein (xi) SEQUENCE DESCRIPTION: SEQ ID NO: 10:

Met Val Arg Ser Ser Ser Arg Thr Pro Ser Asp Lys Pro Val Ala His
1               5               10              15

Val Val Ala Asn Pro Gln Ala Glu Gly Gln Leu Gln Trp Leu Asn Arg
            20              25              30

Arg Ala Asn Ala Leu Leu Ala Asn Gly Val Glu Leu Arg Asp Asn Gln
        35              40              45

Leu Val Val Pro Ser Glu Gly Leu Tyr Leu Ile Tyr Ser Gln Val Leu
    50              55              60

Phe Lys Gly Gln Gly Cys Pro Ser Thr His Val Leu Gln Tyr Ile Lys
65              70              75              80

Ala Asn Ser Lys Phe Ile Gly Ile Thr Glu Leu Val Asn Leu Leu Ser
            85              90              95

Ala Ile Lys Ser Pro Cys Gln Arg Glu Thr Pro Glu Gly Ala Glu Ala
        100             105             110
```

```
Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
130                 135                 140

Phe Ala Glu Ser Gly Gln Val Tyr Phe Gly Ile Ile Ala Leu
145                 150                 155
```

(2) INFORMATION FOR SEQ ID NO: 11:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION:1..474
        (D) OTHER INFORMATION:/codon_start= 1
            /function= "Antigen"
            /product= "TNF-alpha analog"
            /gene= "tnfP30-1"
            /standard_name= "TNF30-1"

(xi) SEQUENCE DESCRIPTION: SEQ ID NO: 11:

```
ATG GTC AGA TCA TCT TCT CGA ACC CCG AGT TTC AAC AAT TTT ACC GTA      48
Met Val Arg Ser Ser Ser Arg Thr Pro Ser Phe Asn Asn Phe Thr Val
160                 165                 170                 175

AGC TTT TGG CTC CGT GTA CCT AAG GTG TCG GCC TCG CAC CTG GAG CGC      96
Ser Phe Trp Leu Arg Val Pro Lys Val Ser Ala Ser His Leu Glu Arg
                180                 185                 190

CGG GCC AAT GCC CTC CTG GCC AAT GGC GTG GAG CTG AGA GAT AAC CAG     144
Arg Ala Asn Ala Leu Leu Ala Asn Gly Val Glu Leu Arg Asp Asn Gln
            195                 200                 205

CTG GTG GTG CCA TCA GAG GGC CTG TAC CTC ATC TAC TCC CAG GTC CTC     192
Leu Val Val Pro Ser Glu Gly Leu Tyr Leu Ile Tyr Ser Gln Val Leu
                210                 215                 220

TTC AAG GGC CAA GGC TGC CCC TCC ACC CAT GTG CTC CTC ACC CAC ACC     240
Phe Lys Gly Gln Gly Cys Pro Ser Thr His Val Leu Leu Thr His Thr
    225                 230                 235

ATC AGC CGC ATC GCC GTC TCC TAC CAG ACC AAG GTC AAC CTC CTC TCT     288
Ile Ser Arg Ile Ala Val Ser Tyr Gln Thr Lys Val Asn Leu Leu Ser
240                 245                 250                 255

GCC ATC AAG AGC CCC TGC CAG AGG GAG ACC CCA GAG GGG GCT GAG GCC     336
Ala Ile Lys Ser Pro Cys Gln Arg Glu Thr Pro Glu Gly Ala Glu Ala
                260                 265                 270

AAG CCC TGG TAT GAG CCC ATC TAT CTG GGA GGG GTC TTC CAG CTG GAG     384
Lys Pro Trp Tyr Glu Pro Ile Tyr Leu Gly Gly Val Phe Gln Leu Glu
            275                 280                 285

AAG GGT GAC CGA CTC AGC GCT GAG ATC AAT CGG CCC GAC TAT CTC GAC     432
Lys Gly Asp Arg Leu Ser Ala Glu Ile Asn Arg Pro Asp Tyr Leu Asp
        290                 295                 300

TTT GCC GAG TCT GGG CAG GTC TAC TTT GGG ATC ATT GCC CTC               474
Phe Ala Glu Ser Gly Gln Val Tyr Phe Gly Ile Ile Ala Leu
    305                 310                 315
```

(2) INFORMATION FOR SEQ ID NO: 12:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 12:

Met Val Arg Ser Ser Ser Arg Thr Pro Ser Phe Asn Asn Phe Thr Val
 1               5                  10                  15

Ser Phe Trp Leu Arg Val Pro Lys Val Ser Ala Ser His Leu Glu Arg
            20                  25                  30

Arg Ala Asn Ala Leu Leu Ala Asn Gly Val Glu Leu Arg Asp Asn Gln
            35                  40                  45

Leu Val Val Pro Ser Glu Gly Leu Tyr Leu Ile Tyr Ser Gln Val Leu
        50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
            115                 120                 125

Lys Gly Asp Arg Leu Ser Ala Glu Ile Asn Arg Pro Asp Tyr Leu Asp
        130                 135                 140

Phe Ala Glu Ser Gly Gln Val Tyr Phe Gly Ile Ile Ala Leu
145                 150                 155

(2) INFORMATION FOR SEQ ID NO: 13:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION:1..474
        (D) OTHER INFORMATION:/codon_start= 1
            /function= "Antigen"
            /product= "TNF-alpha analog"
            /gene= "tnfP30-2"
            /standard_name= "TNF30-2"

(xi) SEQUENCE DESCRIPTION: SEQ ID NO: 13:

```
ATG GTC AGA TCA TCT TCT CGA ACC CCG AGT GAC AAG CCT GTA GCC CAT        48
Met Val Arg Ser Ser Ser Arg Thr Pro Ser Asp Lys Pro Val Ala His
160                 165                 170                 175

GTT GTA GCA AAC CCT CAA GCT GAG GGG CAG CTC CAG TGG CTG AAC CGC        96
Val Val Ala Asn Pro Gln Ala Glu Gly Gln Leu Gln Trp Leu Asn Arg
            180                 185                 190
```

```
CGG GCC AAT GCC CTC CTG GCC AAT TTC AAC AAC TTC ACA GTT AGC TTC         144
Arg Ala Asn Ala Leu Leu Ala Asn Phe Asn Asn Phe Thr Val Ser Phe
            195                 200                 205

TGG TTG AGG GTA CCA AAG GTC TCG GCC AGC CAC CTC GAG CAG GTC CTC         192
Trp Leu Arg Val Pro Lys Val Ser Ala Ser His Leu Glu Gln Val Leu
        210                 215                 220

TTC AAG GGC CAA GGC TGC CCC TCC ACC CAT GTG CTC CTC ACC CAC ACC         240
Phe Lys Gly Gln Gly Cys Pro Ser Thr His Val Leu Leu Thr His Thr
    225                 230                 235

ATC AGC CGC ATC GCC GTC TCC TAC CAG ACC AAG GTC AAC CTC CTC TCT         288
Ile Ser Arg Ile Ala Val Ser Tyr Gln Thr Lys Val Asn Leu Leu Ser
240                 245                 250                 255

GCC ATC AAG AGC CCC TGC CAG AGG GAG ACC CCA GAG GGG GCT GAG GCC         336
Ala Ile Lys Ser Pro Cys Gln Arg Glu Thr Pro Glu Gly Ala Glu Ala
                260                 265                 270

AAG CCC TGG TAT GAG CCC ATC TAT CTG GGA GGG GTC TTC CAG CTG GAG         384
Lys Pro Trp Tyr Glu Pro Ile Tyr Leu Gly Gly Val Phe Gln Leu Glu
            275                 280                 285

AAG GGT GAC CGA CTC AGC GCT GAG ATC AAT CGG CCC GAC TAT CTC GAC         432
Lys Gly Asp Arg Leu Ser Ala Glu Ile Asn Arg Pro Asp Tyr Leu Asp
        290                 295                 300

TTT GCC GAG TCT GGG CAG GTC TAC TTT GGG ATC ATT GCC CTC                 474
Phe Ala Glu Ser Gly Gln Val Tyr Phe Gly Ile Ile Ala Leu
    305                 310                 315
```

(2) INFORMATION FOR SEQ ID NO: 14:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Val Arg Ser Ser Ser Arg Thr Pro Ser Asp Lys Pro Val Ala His
  1               5                  10                  15

Val Val Ala Asn Pro Gln Ala Glu Gly Gln Leu Gln Trp Leu Asn Arg
                20                  25                  30

Arg Ala Asn Ala Leu Leu Ala Asn Phe Asn Asn Phe Thr Val Ser Phe
            35                  40                  45

Trp Leu Arg Val Pro Lys Val Ser Ala Ser His Leu Glu Gln Val Leu
        50                  55                  60

Phe Lys Gly Gln Gly Cys Pro Ser Thr His Val Leu Leu Thr His Thr
 65                 70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
            100                 105                 110

Lys Pro Trp Tyr Glu Pro Ile Tyr Leu Gly Gly Val Phe Gln Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155
```

(2) INFORMATION FOR SEQ ID NO: 15:

(i) SEQUENCE CHARACTERISTICS:
        (A) LENGTH: 474 base pairs (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Homo sapiens (ix) FEATURE:
      (A) NAME/KEY: CDS
      (B) LOCATION:1..474
      (D) OTHER INFORMATION:/codon_start= 1
          /function= "Antigen"
          /product= "TNF-alpha analog"
          /gene= "tnfP30-3"
          /standard_name= "TNF30-3"

(xi) SEQUENCE DESCRIPTION: SEQ ID NO: 15:

```
ATG GTC AGA TCA TCT TCT CGA ACC CCG AGT GAC AAG CCT GTA GCC CAT        48
Met Val Arg Ser Ser Ser Arg Thr Pro Ser Asp Lys Pro Val Ala His
160             165                 170                 175

GTT GTA GCA AAC CCT CAA GCT GAG GGG CAG CTC CAG TGG CTG AAC CGC        96
Val Val Ala Asn Pro Gln Ala Glu Gly Gln Leu Gln Trp Leu Asn Arg
            180                 185                 190

CGG GCC AAT GCC CTC CTG GCC AAT GGC GTG GAG CTG AGA GAT AAC CAG       144
Arg Ala Asn Ala Leu Leu Ala Asn Gly Val Glu Leu Arg Asp Asn Gln
        195                 200                 205

CTG GTG GTG CCA TCA GAG GGC CTG TAC CTC ATC TAC TCC CAG GTC CTC       192
Leu Val Val Pro Ser Glu Gly Leu Tyr Leu Ile Tyr Ser Gln Val Leu
    210                 215                 220

TTC AAC AAC TTT ACC GTC TCC TTC TGG CTT CGG GTA CCC AAG GTC AGC       240
Phe Asn Asn Phe Thr Val Ser Phe Trp Leu Arg Val Pro Lys Val Ser
225                 230                 235

GCT AGC CAC CTC GAG GTC TCC TAC CAG ACC AAG GTC AAC CTC CTC TCT       288
Ala Ser His Leu Glu Val Ser Tyr Gln Thr Lys Val Asn Leu Leu Ser
240                 245                 250                 255

GCC ATC AAG AGC CCC TGC CAG AGG GAG ACC CCA GAG GGG GCT GAG GCC       336
Ala Ile Lys Ser Pro Cys Gln Arg Glu Thr Pro Glu Gly Ala Glu Ala
                260                 265                 270

AAG CCC TGG TAT GAG CCC ATC TAT CTG GGA GGG GTC TTC CAG CTG GAG       384
Lys Pro Trp Tyr Glu Pro Ile Tyr Leu Gly Gly Val Phe Gln Leu Glu
            275                 280                 285

AAG GGT GAC CGA CTC AGC GCT GAG ATC AAT CGG CCC GAC TAT CTC GAC       432
Lys Gly Asp Arg Leu Ser Ala Glu Ile Asn Arg Pro Asp Tyr Leu Asp
        290                 295                 300

TTT GCC GAG TCT GGG CAG GTC TAC TTT GGG ATC ATT GCC CTC               474
Phe Ala Glu Ser Gly Gln Val Tyr Phe Gly Ile Ile Ala Leu
    305                 310                 315
```

(2) INFORMATION FOR SEQ ID NO: 16:

(i) SEQUENCE CHARACTERISTICS:
      (A) LENGTH: 158 amino acids
      (B) TYPE: amino acid
      (D) TOPOLOGY: linear (ii) MOLECULE TYPE: protein (xi) SEQUENCE DESCRIPTION: SEQ ID NO: 16:

```
Met Val Arg Ser Ser Ser Arg Thr Pro Ser Asp Lys Pro Val Ala His
1               5                   10                  15
```

-continued

```
Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
                35                  40                  45

Leu Val Val Pro Ser Glu Gly Leu Tyr Leu Ile Tyr Ser Gln Val Leu
     50                  55                  60

Phe Asn Phe Thr Val Ser Phe Trp Leu Arg Val Pro Lys Val Ser
 65              70                  75                  80

Ala Ser His Leu Glu Val Ser Tyr Gln Thr Lys Val Asn Leu Leu Ser
                85                  90                  95

Ala Ile Lys Ser Pro Cys Gln Arg Glu Thr Pro Glu Gly Ala Glu Ala
                100                 105                 110

Lys Pro Trp Tyr Glu Pro Ile Tyr Leu Gly Gly Val Phe Gln Leu Glu
                115                 120                 125

Lys Gly Asp Arg Leu Ser Ala Glu Ile Asn Arg Pro Asp Tyr Leu Asp
130                 135                 140

Phe Ala Glu Ser Gly Gln Val Tyr Phe Gly Ile Ile Ala Leu
145                 150                 155
```

(2) INFORMATION FOR SEQ ID NO: 17:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION:1..474
        (D) OTHER INFORMATION:/function= "Antigen"
           /product= "TNF-alpha analog"
           /gene= "tnfP30-4"
           /standard_name= "TNF30-4"

(xi) SEQUENCE DESCRIPTION: SEQ ID NO: 17:

```
ATG GTC AGA TCA TCT TCT CGA ACC CCG AGT GAC AAG CCT GTA GCC CAT      48
Met Val Arg Ser Ser Ser Arg Thr Pro Ser Asp Lys Pro Val Ala His
160                 165                 170                 175

GTT GTA GCA AAC CCT CAA GCT GAG GGG CAG CTC CAG TGG CTG AAC CGC      96
Val Val Ala Asn Pro Gln Ala Glu Gly Gln Leu Gln Trp Leu Asn Arg
                180                 185                 190

CGG GCC AAT GCC CTC CTG GCC AAT GGC GTG GAG CTG AGA GAT AAC CAG     144
Arg Ala Asn Ala Leu Leu Ala Asn Gly Val Glu Leu Arg Asp Asn Gln
                195                 200                 205

CTG GTG GTG CCA TCA GAG GGC CTG TAC CTC ATC TAC TCC CAG GTC CTC     192
Leu Val Val Pro Ser Glu Gly Leu Tyr Leu Ile Tyr Ser Gln Val Leu
         210                 215                 220

TTC AAG GGC CAA GGC TGC CCC TCC ACC CAT GTG CTC CTC ACC CAC ACC     240
Phe Lys Gly Gln Gly Cys Pro Ser Thr His Val Leu Leu Thr His Thr
                 225                 230                 235

ATC AGC CGC ATC GCC GTC TCC TAC CAG ACC AAG GTC AAC CTC CTC TCT     288
Ile Ser Arg Ile Ala Val Ser Tyr Gln Thr Lys Val Asn Leu Leu Ser
240                 245                 250                 255
```

```
GCC ATC AAG AGC CCC TGC CAG AGG GAG ACC CCA TTT AAT AAT TTC ACC     336
Ala Ile Lys Ser Pro Cys Gln Arg Glu Thr Pro Phe Asn Asn Phe Thr
            260                 265                 270

GTG TCC TTC TGG TTG CGC GTC CCT AAG GTA AGC GCT TCC CAC CTG GAG     384
Val Ser Phe Trp Leu Arg Val Pro Lys Val Ser Ala Ser His Leu Glu
        275                 280                 285

AAG GGT GAC CGA CTC AGC GCT GAG ATC AAT CGG CCC GAC TAT CTC GAC     432
Lys Gly Asp Arg Leu Ser Ala Glu Ile Asn Arg Pro Asp Tyr Leu Asp
            290                 295                 300

TTT GCC GAG TCT GGG CAG GTC TAC TTT GGG ATC ATT GCC CTC             474
Phe Ala Glu Ser Gly Gln Val Tyr Phe Gly Ile Ile Ala Leu
        305                 310                 315
```

(2) INFORMATION FOR SEQ ID NO: 18:

(i) SEQUENCE CHARACTERISTICS:
        (A) LENGTH: 158 amino acids
        (B) TYPE: amino acid
        (D) TOPOLOGY: linear (ii) MOLECULE TYPE: protein (xi) SEQUENCE DESCRIPTION: SEQ ID NO: 18:

```
Met Val Arg Ser Ser Ser Arg Thr Pro Ser Asp Lys Pro Val Ala His
 1               5                  10                  15

Val Val Ala Asn Pro Gln Ala Glu Gly Gln Leu Gln Trp Leu Asn Arg
            20                  25                  30

Arg Ala Asn Ala Leu Leu Ala Asn Gly Val Glu Leu Arg Asp Asn Gln
        35                  40                  45

Leu Val Val Pro Ser Glu Gly Leu Tyr Leu Ile Tyr Ser Gln Val Leu
    50                  55                  60

Phe Lys Gly Gln Gly Cys Pro Ser Thr His Val Leu Leu Thr His Thr
65                  70                  75                  80

Ile Ser Arg Ile Ala Val Ser Tyr Gln Thr Lys Val Asn Leu Leu Ser
                85                  90                  95

Ala Ile Lys Ser Pro Cys Gln Arg Glu Thr Pro Phe Asn Asn Phe Thr
            100                 105                 110

Val Ser Phe Trp Leu Arg Val Pro Lys Val Ser Ala Ser His Leu Glu
        115                 120                 125

Lys Gly Asp Arg Leu Ser Ala Glu Ile Asn Arg Pro Asp Tyr Leu Asp
    130                 135                 140

Phe Ala Glu Ser Gly Gln Val Tyr Phe Gly Ile Ile Ala Leu
145                 150                 155
```

(2) INFORMATION FOR SEQ ID NO: 19:

(i) SEQUENCE CHARACTERISTICS:
        (A) LENGTH: 474 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION:1..474

(D) OTHER INFORMATION:/codon_start= 1
    /function= "Antigen"
    /product= "TNF-alpha analog"
    /gene= "tnfP30-5"
    /standard_name= "TNF30-5"

(xi) SEQUENCE DESCRIPTION: SEQ ID NO: 19:

| | | | | | | | | | | | | | | | |
|---|---|---|---|---|---|---|---|---|---|---|---|---|---|---|---|
| ATG | GTC | AGA | TCA | TCT | TCT | CGA | ACC | CCG | AGT | GAC | AAG | CCT | GTA | GCC | CAT | 48 |
| Met | Val | Arg | Ser | Ser | Ser | Arg | Thr | Pro | Ser | Asp | Lys | Pro | Val | Ala | His |
| 160 | | | | 165 | | | | | 170 | | | | | 175 | |
| GTT | GTA | GCA | AAC | CCT | CAA | GCT | GAG | GGG | CAG | CTC | CAG | TGG | CTG | AAC | CGC | 96 |
| Val | Val | Ala | Asn | Pro | Gln | Ala | Glu | Gly | Gln | Leu | Gln | Trp | Leu | Asn | Arg |
| | | | | 180 | | | | | 185 | | | | | 190 | |
| CGG | GCC | AAT | GCC | CTC | CTG | GCC | AAT | GGC | GTG | GAG | CTG | AGA | GAT | AAC | CAG | 144 |
| Arg | Ala | Asn | Ala | Leu | Leu | Ala | Asn | Gly | Val | Glu | Leu | Arg | Asp | Asn | Gln |
| | | | 195 | | | | | 200 | | | | | 205 | | |
| CTG | GTG | GTG | CCA | TCA | GAG | GGC | CTG | TAC | CTC | ATC | TAC | TCC | CAG | GTC | CTC | 192 |
| Leu | Val | Val | Pro | Ser | Glu | Gly | Leu | Tyr | Leu | Ile | Tyr | Ser | Gln | Val | Leu |
| | | | 210 | | | | | 215 | | | | | 220 | | |
| TTC | AAG | GGC | CAA | GGC | TGC | CCC | TCC | ACC | CAT | GTG | CTC | CTC | ACC | CAC | ACC | 240 |
| Phe | Lys | Gly | Gln | Gly | Cys | Pro | Ser | Thr | His | Val | Leu | Leu | Thr | His | Thr |
| | 225 | | | | | 230 | | | | | 235 | | | | |
| ATC | AGC | CGC | ATC | GCC | GTC | TCC | TAC | CAG | ACC | AAG | GTC | AAC | CTC | CTC | TCT | 288 |
| Ile | Ser | Arg | Ile | Ala | Val | Ser | Tyr | Gln | Thr | Lys | Val | Asn | Leu | Leu | Ser |
| 240 | | | | | 245 | | | | | 250 | | | | | 255 |
| GCC | ATC | AAG | AGC | CCC | TGC | CAG | AGG | GAG | ACC | CCA | GAG | GGG | GCT | GAG | GCC | 336 |
| Ala | Ile | Lys | Ser | Pro | Cys | Gln | Arg | Glu | Thr | Pro | Glu | Gly | Ala | Glu | Ala |
| | | | | 260 | | | | | 265 | | | | | 270 | |
| AAG | CCC | TGG | TAT | GAG | CCC | ATC | TAT | CTG | GGA | GGG | GTC | TTC | CAG | CTG | GAG | 384 |
| Lys | Pro | Trp | Tyr | Glu | Pro | Ile | Tyr | Leu | Gly | Gly | Val | Phe | Gln | Leu | Glu |
| | | | 275 | | | | | 280 | | | | | 285 | | |
| AAG | GGT | GAC | CGA | TTC | AAC | AAT | TTC | ACC | GTA | AGC | TTC | TGG | CTT | CGC | GTC | 432 |
| Lys | Gly | Asp | Arg | Phe | Asn | Asn | Phe | Thr | Val | Ser | Phe | Trp | Leu | Arg | Val |
| | | | 290 | | | | | 295 | | | | | 300 | | |
| CCT | AAG | GTG | TCT | GCG | TCG | CAC | CTC | GAA | GGG | ATC | ATT | GCC | CTC | | | 474 |
| Pro | Lys | Val | Ser | Ala | Ser | His | Leu | Glu | Gly | Ile | Ile | Ala | Leu | | |
| | 305 | | | | | 310 | | | | | 315 | | | | |

(2) INFORMATION FOR SEQ ID NO: 20:

(i) SEQUENCE CHARACTERISTICS:
    (A) LENGTH: 158 amino acids
    (B) TYPE: amino acid
    (D) TOPOLOGY: linear (ii) MOLECULE TYPE: protein (xi) SEQUENCE DESCRIPTION: SEQ ID NO: 20:

| | | | | | | | | | | | | | | |
|---|---|---|---|---|---|---|---|---|---|---|---|---|---|---|
| Met | Val | Arg | Ser | Ser | Ser | Arg | Thr | Pro | Ser | Asp | Lys | Pro | Val | Ala | His |
| 1 | | | | 5 | | | | | 10 | | | | | 15 | |
| Val | Val | Ala | Asn | Pro | Gln | Ala | Glu | Gly | Gln | Leu | Gln | Trp | Leu | Asn | Arg |
| | | | | 20 | | | | | 25 | | | | | 30 | |
| Arg | Ala | Asn | Ala | Leu | Leu | Ala | Asn | Gly | Val | Glu | Leu | Arg | Asp | Asn | Gln |
| | | | 35 | | | | | 40 | | | | | 45 | | |
| Leu | Val | Val | Pro | Ser | Glu | Gly | Leu | Tyr | Leu | Ile | Tyr | Ser | Gln | Val | Leu |
| | | | 50 | | | | | 55 | | | | | 60 | | |
| Phe | Lys | Gly | Gln | Gly | Cys | Pro | Ser | Thr | His | Val | Leu | Leu | Thr | His | Thr |
| 65 | | | | | 70 | | | | | 75 | | | | | 80 |
| Ile | Ser | Arg | Ile | Ala | Val | Ser | Tyr | Gln | Thr | Lys | Val | Asn | Leu | Leu | Ser |
| | | | | 85 | | | | | 90 | | | | | 95 | |
| Ala | Ile | Lys | Ser | Pro | Cys | Gln | Arg | Glu | Thr | Pro | Glu | Gly | Ala | Glu | Ala |

```
                100             105             110
Lys Pro Trp Tyr Glu Pro Ile Tyr Leu Gly Gly Val Phe Gln Leu Glu
        115                 120                 125

Lys Gly Asp Arg Phe Asn Asn Phe Thr Val Ser Phe Trp Leu Arg Val
    130                 135                 140

Pro Lys Val Ser Ala Ser His Leu Glu Gly Ile Ile Ala Leu
145             150                 155
```

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION:1..24
        (C) IDENTIFICATION METHOD: experimental
        (D) OTHER INFORMATION:/function= "Primer for PCR cloning
            of DNA encoding TNF-alpha"
            /product= "Primer binding to TNF-alpha gene"
            /evidence= EXPERIMENTAL
            /standard_name= "TNF-alpha Primer I"
            /label= Primer1

(xi) SEQUENCE DESCRIPTION: SEQ ID NO: 21:

GACAAGCCCA TGGTCAGATC ATCT                                                    24

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION:1..30
        (C) IDENTIFICATION METHOD: experimental
        (D) OTHER INFORMATION:/function= "Primer for PCR cloning
            of DNA encoding TNF-alpha"
            /product= "Primer binding to TNF-alpha gene"
            /evidence= EXPERIMENTAL
            /standard_name= "TNF-alpha Primer II"
            /label= Primer2

(xi) SEQUENCE DESCRIPTION: SEQ ID NO: 22:

TCTCTAGAGG GCAATGATCC CAAAGTAGAC                                        30

(2) INFORMATION FOR SEQ ID NO: 23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
             (A) NAME/KEY: misc_feature
             (B) LOCATION:1..21
             (C) IDENTIFICATION METHOD: experimental
             (D) OTHER INFORMATION:/function= "Primer for PCR cloning
                 of DNA encoding TNF-alpha"
                 /product= "Primer binding to TNF-alpha gene"
                 /evidence= EXPERIMENTAL
                 /standard_name= "TNF-alpha Primer III"
                 /label= Primer3

(xi) SEQUENCE DESCRIPTION: SEQ ID NO: 23:

CCCAAAGTAG ACCTGCCCAG A                                                      21

(2) INFORMATION FOR SEQ ID NO: 24:

(i) SEQUENCE CHARACTERISTICS:
             (A) LENGTH: 69 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens (ix) FEATURE:
             (A) NAME/KEY: insertion_seq
             (B) LOCATION:7..51
             (C) IDENTIFICATION METHOD: experimental
             (D) OTHER INFORMATION:/function= "Primer for PCR cloning
                 of DNA encoding TNF-alpha analog"
                 /evidence= EXPERIMENTAL
                 /organism= "Homo sapiens"
                 /standard_name= "Primer "mut2-1""
                 /label= mut2-1
                 /note= "Primer "mut2-1" is a synthetically synthesised
                 69-mer oligonucleotide comprising DNA encoding the human
                 T cell epitope P2 between stretches of DNA homologous to
                 stretches of the human TNF-alpha gene"

(xi) SEQUENCE DESCRIPTION: SEQ ID NO: 24:

ACCCCGAGTC AGTACATTAA AGCCAATTCT AAATTCATCG GTATAACTGA GCTGCAGCTC          60

CAGTGGCTG                                                                  69

(2) INFORMATION FOR SEQ ID NO: 25:

(i) SEQUENCE CHARACTERISTICS:
             (A) LENGTH: 73 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Homo sapiens

```
    (ix) FEATURE:
        (A) NAME/KEY: insertion_seq
        (B) LOCATION:15..59
        (C) IDENTIFICATION METHOD: experimental
        (D) OTHER INFORMATION:/function= "Primer for PCR cloning
            of DNA encoding TNF-alpha analog"
            /evidence= EXPERIMENTAL
            /organism= "Homo sapiens"
            /stand -continued (A) NAME/KEY: insertion_seq
        (B) LOCATION:8..52
        (C) IDENTIFICATION METHOD: experimental
        (D) OTHER INFORMATION:/function= "Primer for PCR cloning
            of DNA encoding TNF-alpha analog"
            /evidence= EXPERIMENTAL
            /organism= "Homo sapiens"
            /standard_name= "Primer "mut2-5""
            /label= mut2-5
            /note= "Primer "mut2-5" is a synthetically synthesised
            75-mer oligonucleotide comprising DNA encoding the human
            T cell epitope P2 between stretches of DNA homologous to
            stretches of the human TNF-alpha gene"

(xi) SEQUENCE DESCRIPTION: SEQ ID NO: 27:

GAAGGGTGAC CGACAGTACA TTAAGGCCAA TTCGAAGTTC ATTGGCATCA CTGAGCTGTC      60

TGGGCAGGTC TACTT                                                       75

(2) INFORMATION FOR SEQ ID NO: 28:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: insertion_seq
        (B) LOCATION:14..58
        (C) IDENTIFICATION METHOD: experimental
        (D) OTHER INFORMATION:/function= "Primer for PCR cloning
            of DNA encoding TNF-alpha analog"
            /evidence= EXPERIMENTAL
            /organism= "Homo sapiens"
            /standard_name= "Primer "mut2-7""
            /label= mut2-7
            /note= "Primer "mut2-7" is a synthetically synthesised
            80-mer oligonucleotide comprising DNA encoding the human
            T cell epitope P2 between stretches of DNA homologous to
            stretches of the human TNF-alpha gene"

(xi) SEQUENCE DESCRIPTION: SEQ ID NO: 28:

CACCCATGTG CTCCAGTACA TCAAAGCTAA CTCCAAATTC ATCGGCATCA CCGAACTGGT      60

TAACCTCCTC TCTGCCATCA                                                  80

(2) INFORMATION FOR SEQ ID NO: 29:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: insertion_seq

```
          (B) LOCATION:10..72
          (C) IDENTIFICATION METHOD: experimental
          (D) OTHER INFORMATION:/function= "Primer for PCR cloning
              of DNA encoding TNF-alpha analog"
              /evidence= EXPERIMENTAL
              /organism= "Homo sapiens"
              /standard_name= "Primer "mut30-1""
              /label= mut30-1
              /note= "Primer "mut30-1" is a synthetically synthesised
              96-mer oligonucleotide comprising DNA encoding the human
              T cell epitope P30 between stretches of DNA homologous to
              stretches of the human TNF-alpha gene"

```
        (C) IDENTIFICATION METHOD: experimental
        (D) OTHER INFORMATION:/function= "Primer for PCR cloning
            of DNA encoding TNF-alpha analog"
            /evidence= EXPERIMENTAL
            /organism= "Homo sapiens"
            /standard_name= "Primer "mut30-3""
            /label= mut30-3
            /note= "Primer "mut30-3" is a synthetically synthesised
            100-mer oligonucleotide comprising DNA encoding human T
            cell epitope P30 between stretches of DNA homologous to
            stretches of the human TNF-alpha gene"

(xi) SEQUENCE DESCRIPTION: SEQ ID NO: 31:

CCCAGGTCCT CTTCAACAAC TTTACCGTCT CCTTCTGGCT TCGGGTACCC AAGGTCAGCG      60

CTAGCCACCT CGAGGTCTCC TACCAGACCA AGGTCAACCT                            100

(2) INFORMATION FOR SEQ ID NO: 32:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: insertion_seq
        (B) LOCATION:15..77
        (C) IDENTIFICATION METHOD: experimental
        (D) OTHER INFORMATION:/function= "Primer for PCR cloning
            of DNA encoding TNF-alpha analog"
            /evidence= EXPERIMENTAL
            /organism= "Homo sapiens"
            /standard_name= "Primer "mut30-4""
            /label= mut30-4
            /note= "Primer "mut30-4" is a synthetically synthesised
            100-mer oligonucleotide comprising DNA encoding human T
            cell epitope P30 between stretches of DNA homologous to
            stretches of the human TNF-alpha gene"

(xi) SEQUENCE DESCRIPTION: SEQ ID NO: 32:

AGTCGGTCAC CCTTCTCCAG GTGGGAAGCG CTTACCTTAG GGACGCGCAA CCAGAAGGAC      60

ACGGTGAAAT TATTAAATGG GGTCTCCCTC TGGCAGGGGC                            100

(2) INFORMATION FOR SEQ ID NO: 33:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: insertion_seq
        (B) LOCATION:14..76
        (C) IDENTIFICATION METHOD: experimental
```

(D) OTHER INFORMATION:/function= "Primer for PCR cloning
    of DNA encoding TNF-alpha analog"
    /evidence= EXPERIMENTAL
    /organism= "Homo sapiens"
    /standard_name= "Primer "mut30-5""
    /label= mut30-5
    /note= "Primer "mut30-5" is a synthetically synthesised
    100-mer oligonucleotide comprising DNA encoding human T
    cell epitope P30 between stretches of DNA homologous to
    stretches of the human TNF-alpha gene"

(xi) SEQUENCE DESCRIPTION: SEQ ID NO: 33:

GAAGGGTGAC CGATTCAACA ATTTCACCGT AAGCTTCTGG CTTCGCGTCC CTAAGGTGTC 60

TGCGTCGCAC CTCGAAGGGA TCATTGCCCT CTAGAGTCGA 100

(2) INFORMATION FOR SEQ ID NO: 34:

(i) SEQUENCE CHARACTERISTICS:
(A) LENGTH: 25 amino acids
(B) TYPE: amino acid
(C) STRANDEDNESS: <Unknown>
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Homo sapiens (ix) FEATURE:
(A) NAME/KEY: Peptide
(B) LOCATION:1..25
(D) OTHER INFORMATION:/label= Pep2-1
/note= “Pep2-1 is a synthetically prepared truncated form of a TNF-alpha analog comprising the human T cell epitope P2 and flanking portions of human TNF-alpha”

(xi) SEQUENCE DESCRIPTION: SEQ ID NO: 34:

Ser Arg Thr Pro Ser Gln Tyr Ile Lys Ala Asn Ser Lys Phe Ile Gly
1 5 10 15

Ile Thr Glu Leu Gln Leu Gln Trp Leu
20 25

(2) INFORMATION FOR SEQ ID NO: 35:

(i) SEQUENCE CHARACTERISTICS:
(A) LENGTH: 25 amino acids
(B) TYPE: amino acid
(C) STRANDEDNESS: <Unknown>
(D) TOPOLOGY: linear (ii) MOLECULE TYPE: peptide (iii) HYPOTHETICAL: NO (v) FRAGMENT TYPE: internal (vi) ORIGINAL SOURCE:
(A) ORGANISM: Homo sapiens (ix) FEATURE:
(A) NAME/KEY: Peptide
(B) LOCATION:1..25
(D) OTHER INFORMATION:/label= Pep2-3
/note= “Pep2-3 is a synthetically prepared truncated form of a TNF-alpha analog comprising the human T cell epitope P2 and flanking portions of human TNF-alpha”

(xi) SEQUENCE DESCRIPTION: SEQ ID NO: 35:

```
Ser Gln Val Leu Phe Gln Tyr Ile Lys Ala Asn Ser Lys Phe Ile Gly
1               5                   10                  15

Ile Thr Glu Leu Ile Ser Arg Ile Ala
            20                  25
```

(2) INFORMATION FOR SEQ ID NO: 36:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens (ix) FEATURE:
        (A) NAME/KEY: Peptide
        (B) LOCATION:1..25
        (D) OTHER INFORMATION:/label= Pep2-4
            /note= "Pep2-4 is a synthetically prepared truncated form
            of a TNF-alpha analog comprising the human T cell epitope
            P2 and flanking portions of human TNF-alpha"

(xi) SEQUENCE DESCRIPTION: SEQ ID NO: 36:

```
Ala Glu Ala Lys Pro Gln Tyr Ile Lys Ala Asn Ser Lys Phe Ile Gly
1               5                   10                  15

Ile Thr Glu Leu Gly Asp Arg Leu Ser
            20                  25
```

(2) INFORMATION FOR SEQ ID NO: 37:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens (ix) FEATURE:
        (A) NAME/KEY: Peptide
        (B) LOCATION:1..25
        (D) OTHER INFORMATION:/label= Pep2-5
            /note= "Pep2-5 is a synthetically prepared truncated form
            of a TNF-alpha analog comprising the human T cell epitope
            P2 and flanking portions of human TNF-alpha"

(xi) SEQUENCE DESCRIPTION: SEQ ID NO: 37:

```
Glu Lys Gly Asp Arg Gln Tyr Ile Lys Ala Asn Ser Lys Phe Ile Gly
1               5                   10                  15

Ile Thr Glu Leu Ser Gly Gln Val Tyr
            20                  25
```

(2) INFORMATION FOR SEQ ID NO: 38:

(i) SEQUENCE CHARACTERISTICS:
        (A) LENGTH: 31 amino acids

```
            (B) TYPE: amino acid
            (C) STRANDEDNESS: <Unknown>
            (D) TOPOLOGY: linear (ii) MOLECULE TYPE: peptide (iii) HYPOTHETICAL: NO (v) FRAGMENT TYPE: internal (vi) ORIGINAL SOURCE:
            (A) ORGANISM: Homo sapiens (ix) FEATURE:
            (A) NAME/KEY: Peptide
            (B) LOCATION:1..31
            (D) OTHER INFORMATION:/label= Pep30-1
                /note= "Pep30-1 is a synthetically prepared truncated
                form of a TNF-alpha analog comprising human T cell
                epitope P30 and flanking portions of human TNF-alpha"

(xi) SEQUENCE DESCRIPTION: SEQ ID NO: 38:

Ser Arg Thr Pro Ser Phe Asn Asn Phe Thr Val Ser Phe Trp Leu Arg
1               5                  10                  15

Val Pro Lys Val Ser Ala Ser His Leu Glu Arg Arg Ala Asn Ala
            20                  25                  30

(A) ORGANISM: Homo sapiens (ix) FEATURE:
        (A) NAME/KEY: Peptide
        (B) LOCATION:1..31
        (D) OTHER INFORMATION:/label= Pep30-3
            /note= "Pep30-3 is a synthetically prepared truncated
            form of a TNF-alpha analog comprising the human T cell
            epitope P30 and flanking portions of human TNF-alpha"

(xi) SEQUENCE DESCRIPTION: SEQ ID NO: 40:

```
Tyr Ser Gln Val Leu Phe Asn Asn Phe Thr Val Ser Phe Trp Le

Glu Lys Gly Asp Arg Phe Asn Asn Phe Thr Val Ser Phe Trp Leu Arg
1               5                   10                  15

Val Pro Lys Val Ser Ala Ser His Leu Glu Gly Ile Ile Ala Leu
            20                  25                  30

(2) INFORMATION FOR SEQ ID NO: 43:

(i) SEQUENCE CHARACTERISTICS:
        (A) LENGTH: 1585 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION:1..1585
        (C) IDENTIFICATION METHOD: experimental
        (D) OTHER INFORMATION:/codon_start= 1
            /function= "Antigen"
            /product= "TNF-alpha analog"
            /evidence= EXPERIMENTAL
            /gene= "tnf"
            /standard_name= "TNF"

(xi) SEQUENCE DESCRIPTION: SEQ ID NO: 43:

```
CACACCCTGA CAAGCTGCCA GGCAGGTTCT CTTCCTCTCA CATACTGACC CACGGCTCCA      60

CCCTCTCTCC CCTGGAAAGG ACACCATGAG CACTGAAAGC ATGATCCGGG ACGTGGAGCT     120

GGCCGAGGAG GCGCTCCCCA AGAAGACAGG GGGGCCCCAG GGCTCCAGGC GGTGCTTGTT     180

CCTCAGCCTC TTCTCCTTCC TGATCGTGGC AGGCGCCACC ACGCTCTTCT GCCTGCTGCA     240

CTTTGGAGTG ATCGGCCCCC AGAGGGAAGA GTCCCCCAGG GACCTCTCTC TAATCAGCCC     300

TCTGGCCCAG GCAGTCAGAT CATCTTCTCG AACCCCGAGT GACAAGCCTG TAGCCCATGT     360

TGTAGCAAAC CCTCAAGCTG AGGGGCAGCT CCAGTGGCTG AACCGCCGGG CCAATGCCCT     420

CCTGGCCAAT GGCGTGGAGC TGAGAGATAA CCAGCTGGTG GTGCCATCAG AGGGCCTGTA     480

CCTCATCTAC TCCCAGGTCC TCTTCAAGGG CCAAGGCTGC CCCTCCACCC ATGTGCTCCT     540

CACCCACACC ATCAGCCGCA TCGCCGTCTC CTACCAGACC AAGGTCAACC TCCTCTCTGC     600

CATCAAGAGC CCCTGCCAGA GGGAGACCCC AGAGGGGGCT GAGGCCAAGC CCTGGTATGA     660

GCCCATCTAT CTGGGAGGGG TCTTCCAGCT GGAGAAGGGT GACCGACTCA GCGCTGAGAT     720

CAATCGGCCC GACTATCTCG ACTTTGCCGA GTCTGGGCAG GTCTACTTTG GGATCATTGC     780

CCTGTGAGGA GGACGAACAT CCAACCTTCC CAAACGCCTC CCCTGCCCCA ATCCCTTTAT     840

TACCCCCTCC TTCAGACACC CTCAACCTCT TCTGGCTCAA AAAGAGAATT GGGGGCTTAG     900

GGTCGGAACC CAAGCTTAGA ACTTTAAGCA ACAAGACCAC CACTTCGAAA CCTGGGATTC     960

AGGAATGTGT GGCCTGCACA GTGAAGTGCT GGCAACCACT AAGAATTCAA ACTGGGGCCT    1020

CCAGAACTCA CTGGGGCCTA CAGCTTTGAT CCCTGACATC TGGAATCTGG AGACCAGGGA    1080

GCCTTTGGTT CTGGCCAGAA TGCTGCAGGA CTTGAGAAGA CCTCACCTAG AAATTGACAC    1140

AAGTGGACCT TAGGCCTTCC TCTCTCCAGA TGTTTCCAGA CTTCCTTGAG ACACGGAGCC    1200

CAGCCCTCCC CATGGAGCCA GCTCCCTCTA TTTATGTTTG CACTTGTGAT TATTTATTAT    1260
```

```
TTATTTATTA TTTATTTATT TACAGATGAA TGTATTTATT TGGGAGACCG GGGTATCCTG    1320

GGGGACCCAA TGTAGGAGCT GCCTTGGCTC AGACATGTTT TCCGTGAAAA CGGAGGCTGA    1380

ACAATAGGCT GTTCCCATGT AGCCCCCTGG CCTCTGTGCC TTCTTTTGAT TATGTTTTTT    1440

AAAATATTAT CTGATTAAGT TGTCTAAACA ATGCTGATTT GGTGACCAAC TGTCACTCAT    1500

TGCTGAGGCC TCTGCTCCCC AGGGAGTTGT GTCTGTAATC GGCCTACTAT TCAGTGGCGA    1560

GAAATAAAGG TTGCTTAGGA AAGAA                                          1585
```

(2) INFORMATION FOR SEQ ID NO: 44:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO: 44:

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
    195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

The invention claimed is:

1. A modified human TNFα molecule capable of raising neutralizing antibodies towards wild-type human TNFα following administration of said modified TNFα molecule to a human host, wherein at least one segment of the human TNFα molecule has been substituted by at least one peptide containing an immunodominant T cell epitope or a truncated form of said molecule containing an immunodominant T-cell epitope and one or both flanking regions of the human TNFα molecule comprising at least one TNFα B cell epitope, wherein the substitution is introduced in any one of the strands of the front β-sheet, in any one of the connecting loops or in any one of the B', I, or D strands of the back β-sheet, or in any one of the connecting loops and in any one of the B', I, or D strands of the back β-sheet, and which substitution leads to inactivation of the biological activity of human TNFα and which substitution essentially ensures preservation of the β-sheet structures of the B and G strands, wherein the inserted T cell epitope is promiscuous and immunogenic in a majority of human HLA class II types, wherein the epitope is from Tetanus toxoid, and wherein said modified human TNFα molecule is selected from the group consisting of SEQ ID NO: 4, SEQ ID NO: 8 SEQ ID NO: 10, SEQ ID NO: 14, SEQ ID NO: 16, and SEQ ID NO: 20.

2. The human TNFα according to claim 1, having the amino acid sequence shown in SEQ ID NO: 8.

3. The human TNFα according to claim 1, having the amino acid sequence shown in SEQ ID NO: 10.

4. The human TNFα molecule according to claim 1, having the amino acid sequence shown in SEQ ID NO: 4 or SEQ ID NO: 16.

5. The human TNFα according to claim 1, having the amino acid sequence shown in SEQ ID NO: 20.

6. The human TNFα according to claim 1, having the amino acid sequence shown in SEQ ID NO: 14.

* * * * *

UNITED STATES PATENT AND TRADEMARK OFFICE
CERTIFICATE OF CORRECTION

| | | |
|---|---|---|
| PATENT NO. | : 7,118,750 B1 | Page 1 of 4 |
| APPLICATION NO. | : 09/060294 | |
| DATED | : October 10, 2006 | |
| INVENTOR(S) | : Martin Roland Jensen et al. | |

It is certified that error appears in the above-identified patent and that said Letters Patent is hereby corrected as shown below:

Delete Sheets 1, 8 & 9 of 20, and substitute therefor attached drawings: substitute the following replacement sheets depicting Figures 1a, 5a and 5b for corresponding Figures 1a, 5a and 5b.

Column 6, lines 34 and 41, change "WO 95/05489" to -- 95/05849 --

Column 8, line 30, change "WO 95/05489" to -- 95/05849 --

Column 15, lines 40, 46, 52, 58, and 64, change "20.000xg" to -- 20,000 x g --

Signed and Sealed this

Fifth Day of August, 2008

JON W. DUDAS
*Director of the United States Patent and Trademark Office*

Crystal Structure of TNF

FIG. 5a
TNFα analogs with the P30 epitope inserted
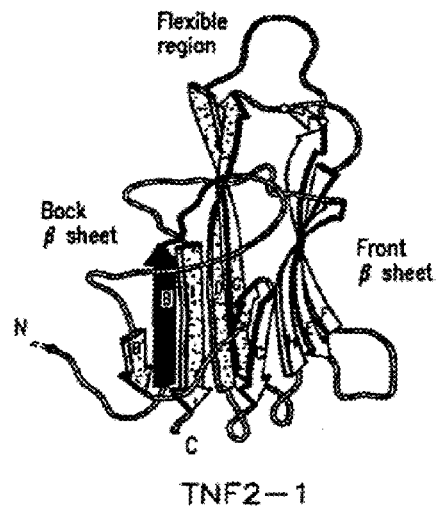
TNF2-1
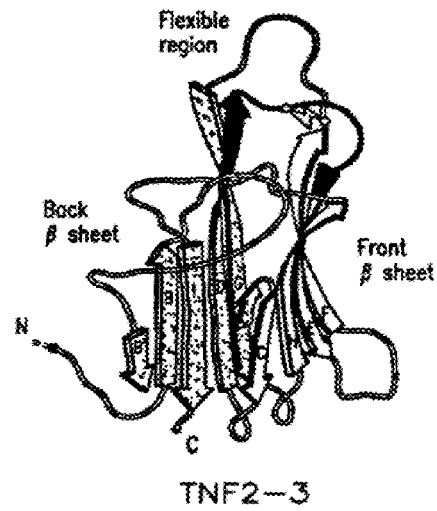
TNF2-3

FIG. 5b
TNFα analogs with the P30 epitope inserted

TNF30-1

TNF30-2

TNF30-3

TNF30-4

TNF30-5